(12) United States Patent
Yang et al.

(10) Patent No.: US 7,858,598 B2
(45) Date of Patent: Dec. 28, 2010

(54) REAGENTS FOR DETECTION OF HYPOCHLOROUS ACID

(75) Inventors: Dan Yang, Hong Kong (CN); Zhen-Ning Sun, Hong Kong (CN); Yan Chen, Hong Kong (CN); Fengqin Liu, Hong Kong (CN)

(73) Assignee: Morningside Ventures Limited & Versitech Limited, Hong Kong (CN)

( * ) Notice: Subject to any disclaimer, the term of this patent is extended or adjusted under 35 U.S.C. 154(b) by 226 days.

(21) Appl. No.: 12/034,670

(22) Filed: Feb. 21, 2008

(65) Prior Publication Data

US 2008/0274560 A1 Nov. 6, 2008

Related U.S. Application Data

(60) Provisional application No. 60/906,788, filed on Mar. 12, 2007.

(51) Int. Cl.
*A01N 55/08* (2006.01)
*A61K 31/69* (2006.01)
*C07H 23/00* (2006.01)

(52) U.S. Cl. .................. 514/64; 548/405; 548/428; 548/429; 544/229; 544/234

(58) Field of Classification Search .................. None
See application file for complete search history.

(56) References Cited

FOREIGN PATENT DOCUMENTS

| JP | 2005 053900 | 3/2005 |
|---|---|---|
| WO | WO 01/64664 | 9/2001 |

OTHER PUBLICATIONS

English abstract of B1, Dated Sep. 7, 2001, Nagano et al.
English abstract of B3, Dated Mar. 3, 2005, Toray Ind Inc.
Bemofsky, C., FASEB J., 1991, 5, 295-300.
Gabe et al., J. Am. Chem. Soc., 2004, vol. 126, No. 10, 3359.
Gould, J. P.; Richards, J. T.; Miles, M. G., Water Res., 1984, 18, 205-212.
Gould, J. P.; Richards, J. T.; Miles, M. G., Water Res., 1984, 18, 991-999.
Hattori et al., J. Phys. Chem. B., 2005, 109, 15368-15375.
Hawkins, C. L.; Davies, M. J., Chem. Res. Toxicol., 2002, 15, 83-92.
Hayatsu, H.; Pan, S.-K.; Ukita, T., Chem. Pharm. Bull., 1971, 19, 2189-2192.
Hazell, L. J.; Stocker, R., Biochem. J., 1993, 290, 165-172.
Hazell, L. J.; van den Berg, J. J.; Stocker, R., Biochem. J., 1994, 302, 297-304.
Hazen, S. L.; Heinecke, J. W., J. Clin. Invest., 1997, 99, 2075-2081.
Hughes, M. N.; Nicklin, H. G., J. Chem. Soc. (A), 1968, 2, 450-452.
Keith, W. G.; Powell, R. E., J. Chem. Soc. (A), 1969, 1, 90.
Lapenna, D.; Cuccurullo, F., Gen. Pharmacol., 1996, 27, 1145-1147.
McKenna, S. M.; Davies, K. J. A., Biochem. J., 1988, 254, 685-692.
Miura et al., J. Am. Chem. Soc., 2003, vol. 125, No. 28, 8667.
Osuka et al., J. Am. Chem. Soc., 1990, 112, 4958-4959.
Owton, J. Chem. Soc., Perkin Trans. 1, 1999, 2409-2420.
Patton, W.; Bacon, V.; Duffield, A. M.; Halpern, B.; Hoyano, Y.; Pereira, W.; Lederberg, J., Biochem. Biophys. Res. Commun., 1972, 48, 880-884.
Prutz, W. A., Arch. Biochem. Biophys., 1996, 332, 110-120.
Prutz, W. A., Arch. Biochem. Biophys., 1998, 349, 183-191.
Prutz, W. A., Arch. Biochem. Biophys., 1999, 371, 107-114.
Sakata et al., J. Am. Chem. Soc., 1994, 116, 6904-6909.
Setsukinai, K.; Urano, Y.; Kakinuma, K.; Nagano, T., J. Biol. Chem. 2003, 278, 3170-3175.
Thomas, E. L., Infect. Immun., 1979, 23, 522-531.
Toyota et al, Langmuir, 2006, 22, 1976-1981.
Vissers, M. C. M.; Winterboum, C. C., Arch. Biochem. Biophys., 1991, 285, 53-59.
Winterbourn, C. C.; Kettle, A. J., Free Radical Biol. Med., 2000, 29, 403-409.
Notification of Transmittal of the International Preliminary Report of PCT/CN2008/000449, mailed on Jun. 12, 2008.
International Search Report of PCT/CN2008/000449, mailed on Jun. 12, 2008.
Written Opinion of PCT/CN2008/000449, mailed on Jun. 12, 2008.

*Primary Examiner*—Yong Chu
*Assistant Examiner*—Michael Barker
(74) *Attorney, Agent, or Firm*—Saliwanchik, Lloyd & Saliwanchik

(57) ABSTRACT

Provided herein are compounds or hypochlorous acid probes which can be used as reagents for measuring, detecting and/or screening, directly or indirectly, hypochlorous acid or hypochlorite. Provided also herein are methods that can be used to measure, directly or indirectly, the amount of hypochlorous acid or hypochlorite in chemical samples and biological samples such as cells and tissues in living organisms. Specifically, the methods include the steps of contacting the hypochlorous acid probes disclosed herein with the samples to form one or more fluorescent compounds, and measuring fluorescence properties of the fluorescent compounds. Provided also herein are high-throughput screening fluorescent methods for detecting or screening hypochlorous acid or compounds that can increase or decrease, directly or indirectly, the level of hypochlorous acid or hypochlorite in chemical and biological samples.

31 Claims, 7 Drawing Sheets

REAGENTS FOR DETECTION OF HYPOCHLOROUS ACID

PRIOR RELATED APPLICATIONS

This application claims priority to U.S. Provisional Patent Application Ser. No. 60/906,788, filed Mar. 12, 2007, which is incorporated herein by reference in its entirety.

FIELD OF THE INVENTION

Provided herein are hypochlorous acid probes which can be used as reagents for measuring, detecting or screening, directly or indirectly, hypochlorous acid or hypochlorite. Also provided herein are methods of making the hypochlorous acid probes and methods of using the hypochlorous acid probes as cell assay agents.

BACKGROUND OF THE INVENTION

Hypochlorite ($OCl^-$) and its protonated form hypochlorous acid (HOCl) has been well known and put to commercial uses (e.g., whitening agent and oxidants) with great success since it was first discovered in 1787. In 1825, the use of calcium hypochlorite for the general sanitation of sewers, privies, morgues, hospital wards, ships, and prisons was reported. Further, since sodium hypochlorite was found to be effective against disease-causing bacteria by the end of the nineteenth century, hypochlorite has been widely used as a universal disinfectant for more than 150 years.

In living organisms, hypochlorite can be synthesized in vivo from hydrogen peroxide and chlorine ions in a chemical reaction catalyzed by the enzyme myeloperoxidase (MPO), which may be secreted by activated phagocytes in zones of inflammation. As a nucleophilic non-radical oxidant, hypochlorite can be used as a microbicidal agent (Thomas, E. L., *Infect. Immun.*, 1979, 23, 522-531). Furthermore, neither bacteria nor normal healthy cells can neutralize its toxic effect because they lack the enzymes required for its catalytic detoxification (Lapenna, D. and Cuccurullo, F., *Gen. Pharmacol.*, 1996, 27, 1145-1147).

Generally, hypochlorite can react with some proteins that may play important roles in killing bacterial cells and/or human diseases (Thomas, E. L., *Infect. Immun.*, 1979, 23, 522-531; McKenna, S. M. and Davies, K. J. A., *Biochem. J.*, 1988, 254, 685-692; Hazell, L. J. and Stocker, R., *Biochem. J.*, 1993, 290, 165-172; Hazell, L. J., van den Berg, J. J. and Stocker, R., *Biochem. J.*, 1994, 302, 297-304). When contacting with proteins, hypochlorite may cause damages to the proteins. For example, hypochlorite may alter protein structures, and/or cause fragmentation and dimerization of proteins. As a strong oxidant, hypochlorite can also oxidize low-density lipoproteins (LDL) rapidly. Furthermore, the reaction of hypochlorite with DNA can also result in both chemical modifications and structural changes in DNA (Hawkins, C. L. and Davies, M. J., *Chem. Res. Toxicol.*, 2002, 15, 83-92; Prutz, W. A., *Arch. Biochem. Biophys.*, 1996, 332, 110-120; *Arch. Biochem. Biophys.*, 1998, 349, 183-191; *Arch. Biochem. Biophys.*, 1999, 371, 107-114).

Because of the above-mentioned uses and roles of hypochlorite and its conjugate acid, i.e., hypochlorous acid, there is a need for methods that detect and measure, directly or indirectly, hypochlorous acid and hypochlorite, including in vivo detection and measurement.

SUMMARY OF THE INVENTION

Provided herein are compounds that can be used as hypochlorous acid probes for measuring, detecting or screening, directly or indirectly, hypochlorous acid or hypochlorite, i.e., the conjugate base of hypochlorous acid. In some embodiments, the hypochlorous acid probes disclosed herein can detect, measure or screen hypochlorous acid selectively and specifically. In other embodiments, the hypochlorous acid probes disclosed herein can selectively react with hypochlorous acid in the presence of other reactive oxygen and/or nitrogen species such as $^1O_2$, NO, $O_2\cdot^-$, $\cdot OH$, $ONOO^-$ and alkylperoxyl radical (ROO$\cdot$). In certain embodiments, the compounds or hypochlorous acid probes are represented by Formula (I):

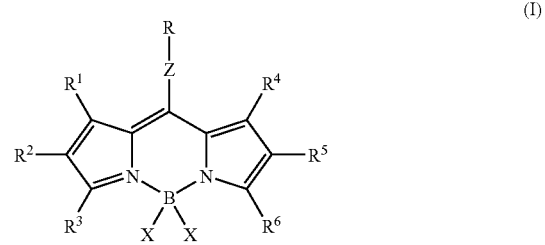

(I)

wherein X is halo;

each of $R^1$, $R^2$, $R^3$, $R^4$, $R^5$ and $R^6$ is independently hydrogen, halo, alkyl, halogenated alkyl, heteroalkyl, alkenyl, alkynyl, aryl, aralkyl, alkaryl, heterocyclyl, cycloalkyl, cycloalkenyl, cycloalkynyl, amino, alkylamino, arylamino, dialkylamino, alkylarylamino, diarylamino, hydroxy, thio, alkoxy, alkylthio, alkoxyalkyl, cyano, nitro, sulfonyl, phosphonyl, sulfonate ester, phosphate ester, —C(=O)—Y or —C(=O)-Q-Y, wherein Y is hydrogen, halo, alkoxy, hydroxy, thio, alkyl, alkenyl, alkynyl, cycloalkyl, cycloalkenyl, cycloalkynyl, aryl, alkaryl, arylalkyl, carbamate, amino, alkylamino, arylamino, dialkylamino, alkylarylamino, diarylamino, alkylthio, heteroalkyl, or heterocyclyl having from 3 to 7 ring atoms; and Q is alkylene, alkenylene, alkynylene, arylene, aralkylene or alkarylene, or $R^1$ and $R^2$ or $R^2$ and $R^3$ or $R^4$ and $R^5$ or $R^5$ and $R^6$ together form a 5-, 6-, or 7-membered cycloalkyl, cycloalkenyl, aryl, heteroalkyl or heteroaryl ring;

Z is a bond or a divalent linking group;

R has one of Formulae (IIIA), (IVA) and (VA):

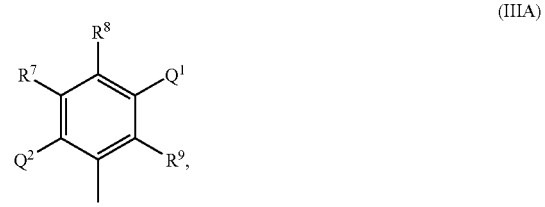

(IIIA)

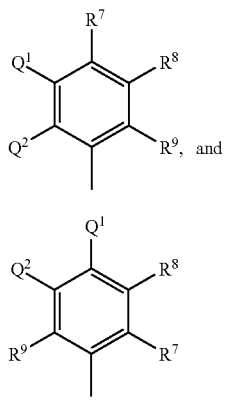

(IVA)

(VA)

wherein each of $R^7$, $R^8$ and $R^9$ is independently hydrogen, halo, alkyl, halogenated alkyl, alkenyl, alkynyl, aryl, aralkyl, alkaryl, heterocyclyl, cycloalkyl, cycloalkenyl, cycloalkynyl, hydroxy, thio, alkoxy, alkylthio, alkoxyalkyl, cyano, nitro, carboxyl, acyl, carbamate, amido, amino, alkylamino, arylamino, dialkylamino, alkylarylamino, diarylamino, or heteroalkyl, or $R^7$ and $R^8$ of Formula (IIIA), (IVA) or (VA) or $R^8$ and $R^9$ of Formula (IVA) together form a 5-, 6-, or 7-membered cycloalkyl, cycloalkenyl, aryl, heteroalkyl or heteroaryl ring; and each of $Q^1$ and $Q^2$ is independently amino or —O-$Q^3$, where $Q^3$ is hydrogen, alkyl, alkenyl, alkoxyalkyl, cycloalkyl, cycloalkenyl, cycloalkynyl, aryl, alkaryl, arylalkyl, alkylamido, alkoxyamido, alkoxycarbonyl, halogenated alkyl or heteroalkyl, with the proviso that $Q^1$ and $Q^2$ are not both amino.

In some embodiments, R is a monovalent dioxygenated aryl group having one of Formulae (IIIB), (IVB) and (VB):

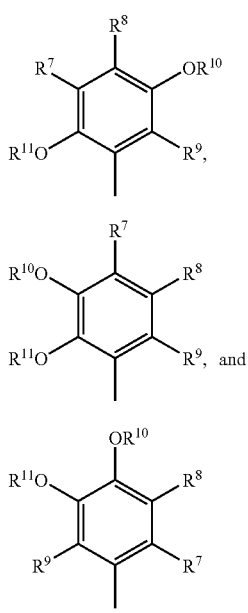

wherein each of $R^7$, $R^8$ and $R^9$ is as defined above; and each of $R^{10}$ and $R^{11}$ is independently hydrogen, alkyl, alkenyl, alkoxyalkyl, cycloalkyl, cycloalkenyl, cycloalkynyl, aryl, alkaryl, arylalkyl, alkylamido, alkoxyamido, alkoxycarbonyl, halogenated alkyl or heteroalkyl.

In some embodiments, X is F. In other embodiments, Z is a bond. In further embodiments, Z is alkylene, alkenylene, alkynylene, heteroalkylene, heteroalkenylene, heteroalkynylene, arylene, or heteroarylene.

In certain embodiments, $R^1$ and $R^2$ together form a 5-, 6- or 7-membered cycloalkyl, cycloalkenyl, aryl, heteroalkyl or heteroaryl ring. In other embodiments, $R^4$ and $R^5$ together form a 5-, 6- or 7-membered cycloalkyl, cycloalkenyl, aryl, heteroalkyl or heteroaryl ring. In further embodiments, $R^2$ and $R^3$ together form a 5-, 6- or 7-membered cycloalkyl, cycloalkenyl, aryl, heteroalkyl or heteroaryl ring. In still further embodiments, $R^5$ and $R^6$ together form a 5-, 6- or 7-membered cycloalkyl, cycloalkenyl, aryl, heteroalkyl or heteroaryl ring. In still further embodiments, $R^7$ and $R^8$ together form a 5-, 6- or 7-membered cycloalkyl, cycloalkenyl, aryl, heteroalkyl or heteroaryl ring.

In certain embodiments, each of $R^3$ and $R^6$ is independently hydrogen or —C(=O)$NR^{12}R^{13}$, wherein each of $R^{12}$ and $R^{13}$ is independently hydrogen, alkyl or aryl. In further embodiments, each of $R^3$ and $R^6$ of Formula (I) is —C(=O)$NR^{12}R^{13}$, wherein each of $R^{12}$ and $R^{13}$ is alkyl. In further embodiments, each of $R^3$ and $R^6$ is —C(=O)N(CH$_2$CH$_3$)$_2$.

In some embodiments, each of $R^{10}$ and $R^{11}$ of any of Formulae (IIIB)-(VB) is independently hydrogen, alkyl, alkenyl, alkoxyalkyl, cycloalkyl, cycloalkenyl, cycloalkynyl, aryl, alkaryl, arylalkyl, alkylamido, alkoxyamido, alkoxycarbonyl, halogenated alkyl or heteroalkyl. In further embodiments, $R^{10}$ is methyl and $R^{11}$ is hydrogen.

In certain embodiments, the compounds or hypochlorous acid probes are represented by Formula (VI):

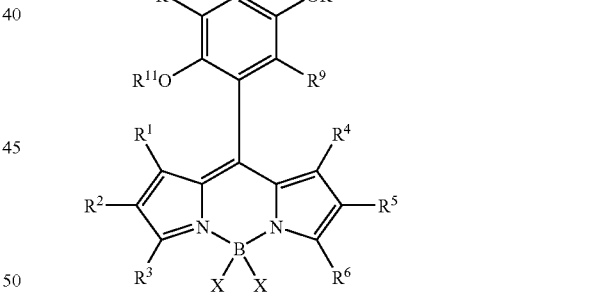

(VI)

wherein X is halo;

each of $R^1$, $R^2$, $R^3$, $R^4$, $R^5$ and $R^6$ is independently hydrogen, halo, alkyl, halogenated alkyl, heteroalkyl, alkenyl, alkynyl, aryl, aralkyl, alkaryl, heterocyclyl, cycloalkyl, cycloalkenyl, cycloalkynyl, amino, alkylamino, arylamino, dialkylamino, alkylarylamino, diarylamino, hydroxy, thio, alkoxy, alkylthio, alkoxyalkyl, cyano, nitro, sulfonyl, phosphonyl, sulfonate ester, phosphate ester, —C(=O)—Y or —C(=O)-Q-Y, wherein Y is hydrogen, halo, alkoxy, hydroxy, thio, alkyl, alkenyl, alkynyl, cycloalkyl, cycloalkenyl, cycloalkynyl, aryl, alkaryl, arylalkyl, carbamate, amino, alkylamino, arylamino, dialkylamino, alkylarylamino, diarylamino, alkylthio, heteroalkyl, or heterocyclyl having from 3 to 7 ring atoms; and Q is alkylene, alkenylene, alkynylene, arylene, aralkylene or alkarylene, or $R^1$ and $R^2$ or $R^7$ and $R^3$ or $R^4$ and $R^5$ or $R^5$ and $R^6$ together form a 5-, 6-, or 7-membered cycloalkyl, cycloalkenyl, aryl, heteroalkyl or heteroaryl ring;

each of $R^7$, $R^8$ and $R^9$ is independently hydrogen, halo, alkyl, halogenated alkyl, alkenyl, alkynyl, aryl, aralkyl, alkaryl, heterocyclyl, cycloalkyl, cycloalkenyl, cycloalkynyl, hydroxy, thio, alkoxy, alkylthio, alkoxyalkyl, cyano, nitro, carboxyl, acyl, carbamate, amido, amino, alkylamino, arylamino, dialkylamino, alkylarylamino, diarylamino, or heteroalkyl, or $R^7$ and $R^8$ together form a 5-, 6-, or 7-membered cycloalkyl, cycloalkenyl, aryl, heteroalkyl or heteroaryl ring; and each of $R^{10}$ and $R^{11}$ is independently hydrogen, alkyl, alkenyl, alkoxyalkyl, cycloalkyl, cycloalkenyl, cycloalkynyl, aryl, alkaryl, arylalkyl, alkylamido, alkoxyamido, alkoxycarbonyl, halogenated alkyl or heteroalkyl.

In other embodiments, the compounds or hypochlorous acid probes are represented by Formula (VII) or (VIII):

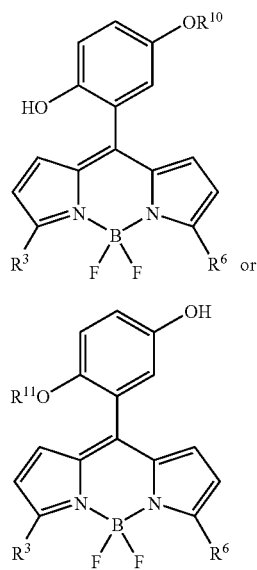

(VII)

(VIII)

wherein $R^{10}$ is alkyl; $R^{11}$ is alkyl; and each of $R^3$ and $R^6$ is independently hydrogen or C(=O)—Y, wherein Y is hydrogen, alkoxy, hydroxy, thio, alkyl, alkenyl, alkynyl, cycloalkyl, cycloalkenyl, cycloalkynyl, aryl, alkaryl, arylalkyl, amino, alkylamino, arylamino, dialkylamino, alkylarylamino, diarylamino, alkylthio, or 3- to 7-membered heterocyclyl ring. In some embodiments, each of $R^3$ and $R^1$ is —C(=O)NR$^{12}$R$^{13}$ wherein each of $R^{12}$ and $R^{13}$ is alkyl.

In other embodiments, the hypochlorous acid probe is Compound (5) or (6), or an isomer thereof.

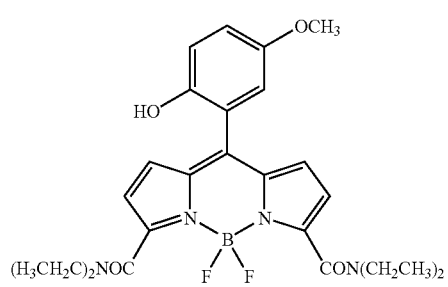

(5)

or

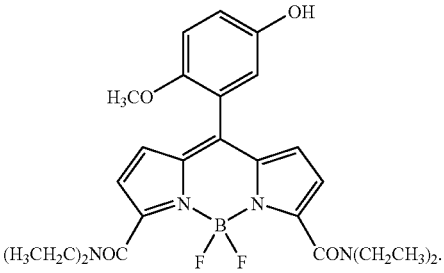

(6)

Provided also herein are compositions for measuring hypochlorous acid in a sample, wherein the compositions comprise the hypochlorous acid probe disclosed herein. In some embodiments, the compositions further comprise a solvent, an acid, a base, a buffer solution or a combination thereof.

Provided also herein are methods for measuring hypochlorous acid in a sample, wherein the methods comprise the steps of:

a) contacting a hypochlorous acid probe disclosed herein with the sample to form a fluorescent compound; and b) measuring fluorescence properties of the fluorescent compound to determine the amount of hypochlorous acid in the sample.

In some embodiments, the sample is a chemical sample or biological sample. In other embodiments, the sample is a biological sample comprising a microorganism, or a cell or tissue from animals.

Provided also herein are high-throughput screening fluorescent methods for detecting hypochlorous acid in samples, wherein the high-throughput methods comprise the steps of:

a) contacting a hypochlorous acid probe disclosed herein with the samples to form one or more fluorescent compounds; and b) measuring fluorescence properties of the fluorescent compounds to determine the amount of hypochlorous acid in the samples.

Provided also herein are high-throughput methods for screening one or more target compounds that can increase or decrease the level of hypochlorous acid, wherein the high-throughput methods comprise the steps of:

a) contacting a hypochlorous acid probe disclosed herein with the target compounds to form one or more fluorescent compounds; and b) measuring fluorescence properties of the fluorescent compounds to determine the target compounds qualitatively or quantitatively.

Provided also herein are methods of preparing the compounds or hypochlorous acid probes of Formula (I) comprising the steps of:

a) reacting pyrroles of Formula (IXA) and (IXB):

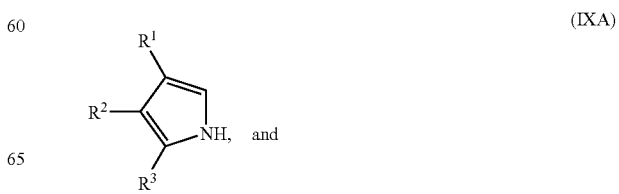

(IXA)

and

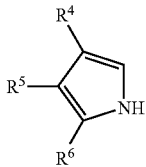

in the presence of an acid catalyst with an aldehyde of Formula (X):

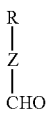

b) adding benzoquinone to the reaction mixture to form a dipyrrole of Formula (XI):

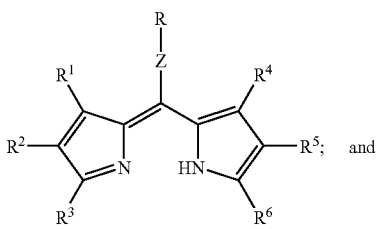

c) reacting the dipyrrole of Formula (XI) with a boron trihalide etherate and triethylamine, wherein each of X, R, Z, $R^1$, $R^2$, $R^3$, $R^4$, $R^5$ and $R^6$ is as defined above.

DEFINITIONS

Figure 1:
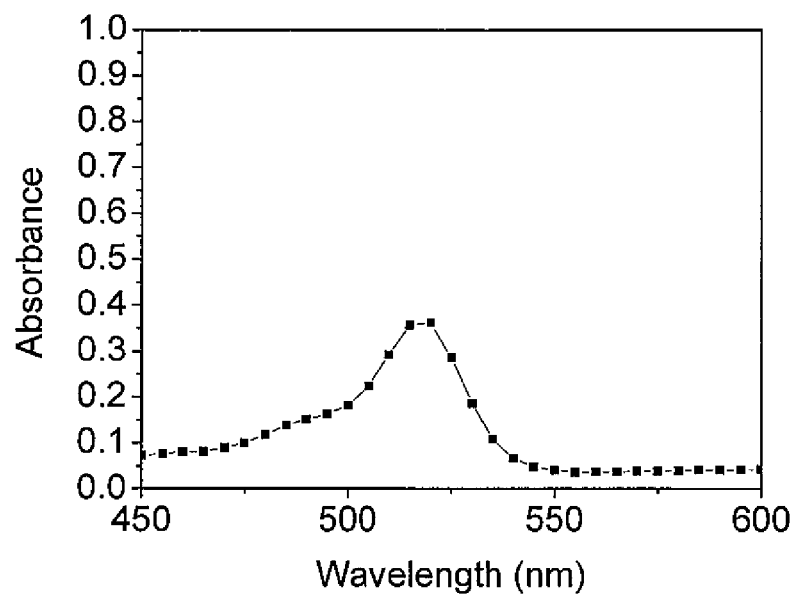
FIG. 1 depicts a UV-visible absorption spectrum of a 10 mM solution of Compound 5 in dichloromethane measured at 25° C.

To facilitate the understanding of the subject matter disclosed herein, a number of terms, abbreviations or other shorthand as used herein are defined below. Any term, abbreviation or shorthand not defined is understood to have the ordinary meaning used by a skilled artisan contemporaneous with the submission of this application.

"Amino" refers to a primary, secondary, or tertiary amine which may be optionally substituted. Specifically included are secondary or tertiary amine nitrogen atoms which are members of a heterocyclic ring. Also specifically included, for example, are secondary or tertiary amino groups substituted by an acyl moiety. Some non-limiting examples of amino group include —$NR^{14}R^{15}$ wherein each of $R^{14}$ and $R^{15}$ is independently H, alkyl, aryl, aralkyl, alkaryl, cycloalkyl, acyl, heteroalkyl, heteroaryl or heterocycyl.

"Alkyl" refers to a fully saturated acyclic monovalent radical containing carbon and hydrogen, and which may be branched or a straight chain. In some embodiments, alkyl contains from about 1 to about 25 carbon atoms. Examples of alkyl groups are methyl, ethyl, n-propyl, isopropyl, n-butyl, t-butyl, n-heptyl, n-hexyl, n-octyl, and n-decyl. "Lower alkyl" refers to an alkyl radical of one to six carbon atoms, as exemplified by methyl, ethyl, n-butyl, i-butyl, t-butyl, isoamyl, n-pentyl, and isopentyl.

"Heteroalkyl" refers to an alkyl group having one or more of the carbon atoms within the alkyl group substituted by a heteroatom such as O, S and N. In some embodiments, the heteroalkyl group comprises one or more O atoms. In other embodiments, the heteroalkyl group comprises one or more S atoms. In further embodiments, the heteroalkyl group comprises one or more aminylene groups. In certain embodiments, the heteroalkyl group comprises two or more O, S, aminylene or a combination thereof.

"Alkenyl" or "alkenylene" respectively refers to a monovalent or divalent hydrocarbyl radical which has at least one double bond. The alkenyl or alkenylene group may be cyclic, branched acyclic or straight acyclic. In some embodiments, the alkenyl or alkenylene group contains only one double bond. In other embodiments, the alkenyl or alkenylene group contains two or more double bonds. In further embodiments, the alkenyl or alkenylene group can be a lower alkenyl or alkenylene containing from two to eight carbon atoms in the principal chain. In further embodiments, the alkenyl or alkenylene group can have one double bond and up to 25 carbon atoms, as exemplified by ethenyl, propenyl, isopropenyl, butenyl, isobutenyl, hexenyl, and the like.

"Alkynyl" or "alkynylene" respectively refers to a monovalent or divalent hydrocarbyl radical which has at least a triple bond. In some embodiments, the alkynyl or alkynylene group contains only one triple bond. In other embodiments, the alkynyl or alkynylene group contains two or more triple bonds. In further embodiments, the alkynyl or alkynylene group can be a lower alkynyl or alkynylene containing from two to eight carbon atoms in the principal chain. In further embodiments, the alkynyl or alkynylene group can have one triple bond and up to 20 carbon atoms, as exemplified by ethynyl, propynyl, isopropynyl, butynyl, isobutynyl, hexynyl, and the like.

"Aromatic" or "aromatic group" refers to aryl or heteroaryl.

"Aryl" refers to optionally substituted carbocyclic aromatic groups. In some embodiments, the aryl group includes a monocyclic or bicyclic group containing from 6 to 12 carbon atoms in the ring portion, such as phenyl, biphenyl, naphthyl, substituted phenyl, substituted biphenyl or substituted naphthyl. In other embodiments, the aryl group is phenyl or substituted phenyl.

"Aralkyl" refers to an alkyl group which is substituted with an aryl group. Some non-limiting examples of aralkyl include benzyl and phenethyl.

"Alkaryl" refers to an aryl group which is substituted with an alkyl group. Some non-limiting examples of alkaryl include methylphenyl and methylnaphthyl.

"Acyl" refers to a monovalent group of the formula —C(=O)H, —C(=O)-alkyl, —C(=O)-aryl, —C(=O)-aralkyl, or —C(=O)-alkaryl.

"Halogen" or "halo" refers to fluorine, chlorine, bromine and iodine.

"Heteroatom" refers to atoms other than carbon and hydrogen.

"Heterocyclo" or "heterocyclyl" refers to optionally substituted, fully saturated or unsaturated, monocyclic or bicyclic, aromatic or nonaromatic groups having at least one heteroatom, such as O, S, N, B and P, in at least one ring. The aromatic heterocyclyl (i.e., heteroaryl) group can have 1 or 2 oxygen atoms, 1 or 2 sulfur atoms, and/or 1 to 4 nitrogen atoms in the ring, and may be bonded to the remainder of the molecule through a carbon or heteroatom. Some non-limiting examples of heteroaryl include furyl, thienyl, thiazolyl, pyridyl, oxazolyl, pyrrolyl, indolyl, quinolinyl, or isoquinolinyl and the like.

"Hydrocarbon" or "hydrocarbyl" refers to organic compounds or radicals consisting exclusively of the elements carbon and hydrogen. Hydrocarbyl includes alkyl, alkenyl, alkynyl, and aryl moieties. Hydrocarbyl also includes alkyl, alkenyl, alkynyl, and aryl moieties substituted with other aliphatic, cyclic or aryl hydrocarbon groups, such as alkaryl, alkenaryl and alkynaryl. In some embodiments, "hydrocarbon" or "hydrocarbyl" comprises 1 to 30 carbon atoms.

"Hydrocarbylene" refers to a divalent group formed by removing two hydrogen atoms from a hydrocarbon, the free valencies of which are not engaged in a double bond, e.g. arylene, alkylene, alkenylene, alkynylene, aralkylene or alkarylene.

"Substituted" as used herein to describe a compound or chemical moiety refers to that at least one hydrogen atom of that compound or chemical moiety is replaced with a second chemical moiety. Non-limiting examples of substituents are those found in the exemplary compounds and embodiments disclosed herein, as well as halogen; alkyl; heteroalkyl; alkenyl; alkynyl; aryl, aryl heteroaryl, hydroxy; alkoxyl; amino; nitro; thiol; thioether; imine; cyano; amido; phosphonato; phosphine; carboxyl; thiocarbonyl; sulfonyl; sulfonamide; ketone; aldehyde; ester; oxo; haloalkyl (e.g., trifluoromethyl); carbocyclic cycloalkyl, which can be monocyclic or fused or non-fused polycyclic (e.g., cyclopropyl, cyclobutyl, cyclopentyl or cyclohexyl) or a heterocycloalkyl, which can be monocyclic or fused or non-fused polycyclic (e.g., pyrrolidinyl, piperidinyl, piperazinyl, morpholinyl or thiazinyl); carbocyclic or heterocyclic, monocyclic or fused or non-fused polycyclic aryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl or benzofuranyl); amino (primary, secondary or tertiary); o-lower alkyl; o-aryl, aryl; aryl-lower alkyl; —CO$_2$CH$_3$; —CONH$_2$; —OCH$_2$CONH$_2$; —NH$_2$; —SO$_2$NH$_2$; —OCHF$_2$; —CF$_3$; —OCF$_3$; —NH(alkyl); —N(alkyl)$_2$; —NH(aryl); —N(alkyl)(aryl); —N(aryl)$_2$; —CHR; —CO(alkyl); —CO(aryl); —CO$_2$(alkyl); and —CO$_2$(aryl); and such moieties can also be optionally substituted by a fused-ring structure or bridge, for example —OCH$_2$O—. These substituents can optionally be further substituted with a substituent selected from such groups. All chemical groups disclosed herein can be substituted, unless it is specified otherwise. For example, "substituted" alkyl, alkenyl, alkynyl, aryl, hydrocarbyl or heterocyclo moieties described herein are moieties which are substituted with a hydrocarbyl moiety, a substituted hydrocarbyl moiety, a heteroatom, or a heterocyclo. Further, substituents may include moieties in which a carbon atom is substituted with a heteroatom such as nitrogen, oxygen, silicon, phosphorus, boron, sulfur, or a halogen atom. These substituents may include halogen, heterocyclo, alkoxy, alkenoxy, alkynoxy, aryloxy, hydroxy, protected hydroxy, keto, acyl, acyloxy, nitro, amino, amido, cyano, thiol, ketals, acetals, esters and ethers.

"Fluorophore" refers to a part of a molecule that causes a molecule to be fluorescent. In general, it is a functional group that can absorb radiation of a specific wavelength and re-emit radiation at a different specific wavelength. The intensity and wavelength of the emitted radiation generally depend on both the fluorophore and the chemical environment of the fluorophore.

"Quinone" refers to an aromatic compound having two carbonyl groups in the same six-membered ring. Some non-limiting examples of quinones include 1,4-benzoquinone, 1,2-benzoquinone, 1,4-naphthoquinone, anthraquinone, phenanthraquinone, and the like.

"Electron acceptor" refers to a compound that accepts at least an electron transferred to it from another compound, generally an electron donor.

"Electron donor" refers to a compound that donates at least an electron to another compound, generally an electron acceptor.

"Hypochlorous acid probes" refers to a compound that can react with hypochlorous acid to form a fluorescent compound. In some embodiments, the hypochlorous acid probes disclosed herein do not react substantially with reactive oxygen species and reactive nitrogen species. In other embodiments, the hypochlorous acid probes disclosed herein may react substantially with reactive oxygen species and reactive nitrogen species.

"Reactive oxygen species" or ROS refer to oxygen-containing ions, free radicals as well as non-radical species. Some non-limiting examples of reactive oxygen species include $^1O_2$, $O_2.^-$, ROO., .OH, OCl$^-$ and $H_2O_2$.

"Reactive nitrogen species" or RNS refer to nitrogen-containing ions, free radicals as well as non-radical species. Some non-limiting examples of reactive nitrogen species include nitric oxide (NO.), nitrogen dioxide ($NO_2$.), nitrite ($NO_2^-$), and peroxynitrite ($ONOO^-$).

"Reacting", "adding" or the like refers to contacting one reactant, reagent, solvent, catalyst, reactive group or the like with another reactant, reagent, solvent, catalyst, reactive group or the like. Reactants, reagents, solvents, catalysts, reactive group or the like can be added individually, simultaneously or separately and can be added in any order. They can be added in the presence or absence of heat and can optionally be added under an inert atmosphere. In some embodiments, "reacting" refers to in situ formation or intra-molecular reaction where the reactive groups are in the same molecule.

"Substantially react" refers to that at least a reactant of a reaction is consumed by an amount of more than about 75% by mole, by more than about 80% by mole, by more than about 85% by mole, or by more than about 90% by mole. In some embodiments, "substantially react" refers to that the reactant is consumed by more than about 95% by mole. In other embodiments, "substantially react" refers to that the reactant is consumed by more than about 97% by mole. In further embodiments, "substantially react" refers to that the reactant is consumed by more than about 99% by mole.

"High-throughput method" refers to a method that can autonomously process or evaluate a large number of samples. In some embodiments, informatics systems can be used and implemented in the high-throughput method. The informatics systems can provide the software control of the physical devices used in the high-throughput method, as well as organize and store electronic data generated by the high-throughput method.

DETAILED DESCRIPTION OF THE INVENTION

Provided herein are compounds that can used as hypochlorous acid probes for detecting, measuring and/or screening hypochlorous acid specifically and/or selectively. The compounds or hypochlorous acid probes generally can be represented by the formula:

D-L-A wherein D is an electron donor; A is an electron acceptor; and L is a bond or a divalent linking group.

In some embodiments, L is a bond. In other embodiments, L is a divalent linking group such as O, S, an aminylene group (e.g., a —NR— group where R is hydrogen, alkyl, alkenyl, alkynyl, carboxyl, acyl, aryl, or heterocyclyl), sulfonyl, an organic linking group, or a combination thereof. The organic linking group disclosed herein may be a divalent organic linking group connecting two fragments (e.g., D and A groups) of a molecule together. Some non-limiting examples of the divalent organic linking group include carbonyl, alkylene, alkenylene, alkynylene, arylene, aralkylene, alkarylene, heteroalkylene, heteroarylene, and combinations thereof. Another non-limiting example of the divalent organic linking group includes a —(CH$_2$)$_m$— group, where m is an integer between 1 and 20, inclusive, and one or more of the methylene groups is optionally replaced by O, S, N, C, B, Si, P, C=O, O=S=O, heterocyclylene, arylene, an NR$_a$ group, a CR$_b$ group, a CR$_c$R$_d$ group, a SiR$_e$R$_f$ group, a BR$_g$, group, or a P(=O)R$_h$ group, where R$_a$, R$_b$, R$_e$, R$^f$, R$_e$, R$_f$, R$_g$, and R$_h$ are, each independently, a bond, hydrogen, hydroxy, thio, carboxyl, amino, halo, acyl, alkoxy, alkylsulfanyl, alkenyl, such as vinyl, allyl, and a 2-phenylethenyl group, alkynyl, heterocyclyl, aryl, a part of a ring group, such as cycloalkyl, heterocyclyl, and benzo, or alkyl where one or more of the hydrogens of the alkyl group is optionally replaced by aryl, hydroxy, thio, carboxyl, amino or halo.

In some embodiments, the electron donor D is a fluorophore group. Some non-limiting examples of suitable fluorophore groups include boron dipyrrimethene group or monovalent groups derived by removing one hydrogen from substituted or unsubstituted fluorescein, porphyrins, sulforhodamines, acridine orange, acridine yellow, auramine O, euxanthin, luciferin, benzanthrone, 9,10-bis(phenylethynyl) anthracene, 5,12-bis(phenylethynyl)naphthacene, calcein, carboxyfluorescein, 1-chloro-9,10-bis(phenylethynyl)anthracene, coumarins such as 7-hydroxycoumarin, cyanine, 4',6-diamidino-2-phenylindole, ethidium bromide, perylene, phycobilins, phycocrythrin, phycoerythrobilin, rhodamine, rubrene, stilbene, Texas Red, green fluorescent protein, yellow fluorescent protein or a derivative thereof.

In certain embodiments, the fluorescence compounds disclosed herein can be represented by the formula D-L-A wherein A is an electron acceptor; L is a bond or a linking group; and D is a boron dipyrrimethene group having Formula (II):

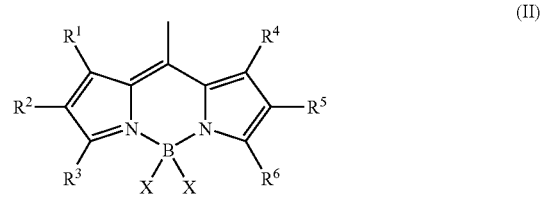

(II)

wherein X is halo; and
each of $R^1$, $R^2$, $R^3$, $R^4$, $R^5$ and $R^6$ is independently hydrogen, halo, alkyl, halogenated alkyl, heteroalkyl, alkenyl, alkynyl, aryl, aralkyl, alkaryl, heterocyclyl, cycloalkyl, cycloalkenyl, cycloalkynyl, amino, alkylamino, arylamino, dialkylamino, alkylarylamino, diarylamino, hydroxy, thio, alkoxy, alkylthio, alkoxyalkyl, cyano, nitro, sulfonyl, phosphonyl, sulfonate ester, phosphate ester, —C(=O)—Y or —C(=O)-Q-Y, wherein Y is hydrogen, halo, alkoxy, hydroxy, thio, alkyl, alkenyl, alkynyl, cycloalkyl, cycloalkenyl, cycloalkynyl, aryl, alkaryl, arylalkyl, carbamate, amino, alkylamino, arylamino, dialkylamino, alkylarylamino, diarylamino, alkylthio, heteroalkyl, or heterocyclyl having from 3 to 7 ring atoms; and Q is alkylene, alkenylene, alkynylene, arylene, aralkylene or alkarylene, or $R^1$ and $R^2$ or $R^2$ and $R^3$ or $R^4$ and $R^5$ or $R^5$ and $R^6$ together form a 5-, 6-, or 7-membered cycloalkyl, cycloalkenyl, aryl, heteroalkyl or heteroaryl ring. In some embodiments, each of $R^3$ and $R^6$ of Formula (II) is independently hydrogen or —C(=O)NR$^{12}$R$^{13}$, wherein each of $R^{12}$ and $R^{13}$ is independently hydrogen, alkyl or aryl. In further embodiments, each of $R^3$ and $R^6$ of Formula (II) is —C(=O)NR$^{12}$R$^{13}$, wherein each of $R^{12}$ and $R^{13}$ is alkyl. In further embodiments, each of $R^3$ and $R^6$ is —C(=O)N(CH$_2$CH$_3$)$_2$.

In other embodiments, A is a monovalent dioxygenated aryl group that can react with hypochlorous acid to form a quinone such as 1,4-benzoquinone, 1,2-benzoquinone, 1,4-naphthoquinone, anthraquinone, phenanthraquinone, and the like. In further embodiments, A has one of Formulae (IIIA), (IVA) and (VA):

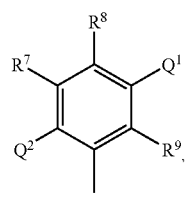

(IIIA)

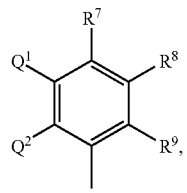

(IVA)

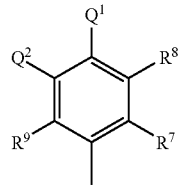

(VA)

wherein each of $R^7$, $R^8$ and $R^9$ is independently hydrogen, halo, alkyl, halogenated alkyl, alkenyl, alkynyl, aryl, aralkyl, alkaryl, heterocyclyl, cycloalkyl, cycloalkenyl, cycloalkynyl, hydroxy, thio, alkoxy, alkylthio, alkoxyalkyl, cyano, nitro, carboxyl, acyl, carbamate, amido, amino, alkylamino, arylamino, dialkylamino, alkylarylamino, diarylamino, or heteroalkyl, or $R^7$ and $R^8$ of Formula (IIIA), (IVA) or (VA) or $R^8$ and $R^9$ of Formula (IVA) together form a 5-, 6-, or 7-membered cycloalkyl, cycloalkenyl, aryl, heteroalkyl or heteroaryl ring; and each of $Q^1$ and $Q^2$ is an electron-donating group. In some embodiments, each of $Q^1$ and $Q^2$ is independently amino or —O-$Q^3$, where $Q^3$ is hydrogen, alkyl, alkenyl, alkoxyalkyl, cycloalkyl, cycloalkenyl, cycloalkynyl, aryl, alkaryl, arylalkyl, alkylamido, alkoxyamido, alkoxycarbonyl, halogenated alkyl or heteroalkyl, with the proviso that $Q^1$ and $Q^2$ are not both amino. In further embodiments, each of $Q^1$ and $Q^2$ is —O-$Q^3$. In further embodiments, $Q^1$ is —O— $Q^3$ and $Q^2$ is amino. In further embodiments, $Q^1$ is amino and $Q^2$ is —O-$Q^3$.

In certain embodiments, R is a monovalent dioxygenated aryl group having one of Formulae (IIIB), (IVB) and (VB):

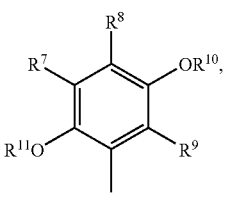

(IIIB)

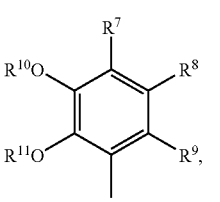

(IVB)

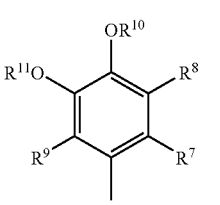

(VB)

wherein each of $R^7$, $R^8$ and $R^9$ is as defined herein; and each of $R^{10}$ and $R^{11}$ is independently hydrogen or an electron-donating group. In some embodiments, each of $R^{10}$ and $R^{11}$ is independently hydrogen, alkyl, alkenyl, alkoxyalkyl, cycloalkyl, cycloalkenyl, cycloalkynyl, aryl, alkaryl, arylalkyl, alkylamido, alkoxyamido, alkoxycarbonyl, halogenated alkyl or heteroalkyl.

In some embodiments, $R^7$ and $R^8$ of Formula (IIIA), (IVA), (VA), (IIIB), (IVB), or (VB) together form a ring. In other embodiments, the $R^7$ and $R^8$ together form a 5-, 6- or 7-membered cycloalkyl, cycloalkenyl, aryl, heteroalkyl or heteroaryl ring. In further embodiments, the $R^7$ and $R^8$ together form a benzo, naphtha, anthrax, pyrido, pyridazino, pyrimido, pyrazino, triazino, tetrazino, pyrazolo, triazolo, or pyrrolo ring. In certain embodiments, the $R^7$ and $R^8$ together form a benzo ring.

In certain embodiments, $R^8$ and $R^9$ of Formula (IVA) or (IVB) together form a ring. In some embodiments, the $R^8$ and $R^9$ together form a 5-, 6- or 7-membered cycloalkyl, cycloalkenyl, aryl, heteroalkyl or heteroaryl ring. In other embodiments, the $R^8$ and $R^9$ together form a benzo, naphtha, anthrax, pyrido, pyridazino, pyrimido, pyrazino, triazino, tetrazino, pyrazolo, triazolo, or pyrrolo ring. In further embodiments, the $R^8$ and $R^9$ together form a benzo ring.

The monovalent dioxygenated aryl group of Formula (IIIB), (IVB) or (VB) can react with hypochlorous acid to form quinone (IIIC), (IVC) or (VC) respectively as shown in Scheme (A) below.

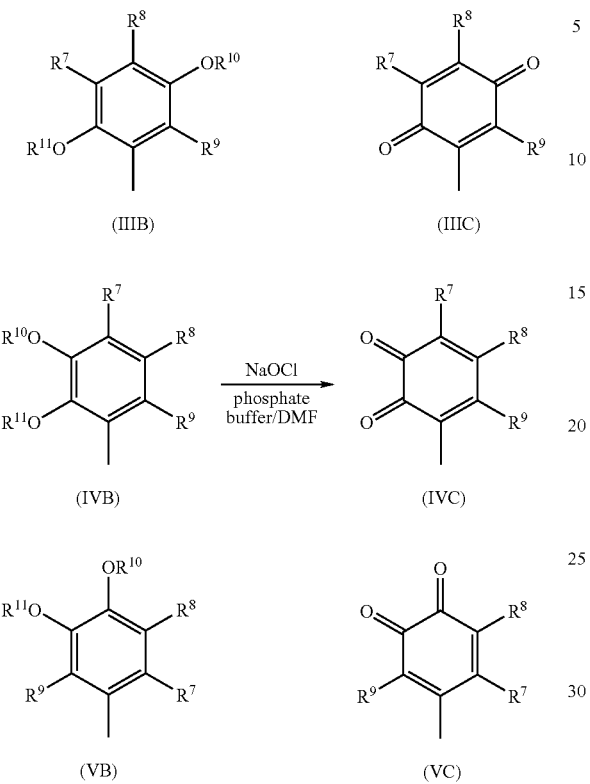

Scheme (A)

(IIIB) (IIIC)

(IVB) → NaOCl phosphate buffer/DMF → (IVC)

(VB) (VC)

In some embodiments, $R^{10}$ is a protected or unprotected hydroxyl group and $R^{11}$ is alkoxy such as methoxy. In other embodiments, $R^{11}$ is a protected or unprotected hydroxyl group and $R^{10}$ is alkoxy such as methoxy. In further embodiments, the dioxygenated aryl group of Formula (IIIB), (IVB) or (VB) in Scheme (A) can be oxidized by hypochlorous acid at room temperature in a pH range from about 7.4 to about 8.2 to form quinone (IIIC), (IVC) or (VC) respectively.

In other embodiments, A is a 1,4- or 1,2-disubstituted arylene or heteroarylene group, wherein the substituents are independently an alkoxy group or a protected or unprotected hydroxyl group. In further embodiments, the arylene group is phenylene.

Further, the compounds or hypochlorous acid probes disclosed herein comprise boron dipyrromethene (BODIPY)-type fluorophores. In some embodiments, the compounds or hypochlorous acid probes represented by general Formulae (I), (VI), (VII) and (VIII) are substantially non-fluorescent. In other embodiments, the compounds or hypochlorous acid probes represented by general Formulae (I), (VI), (VII) and (VIII) can efficiently reacted with hypochlorous acid under physiological conditions to give a strong fluorescent signal. In further embodiments, the amount of hypochlorous acid can be determined with very high specificity and selectivity by measuring the fluorescent signal of the oxidized hypochlorous acid probes.

In some embodiments, the compounds or hypochlorous acid probes disclosed herein are represented by Formula (I):

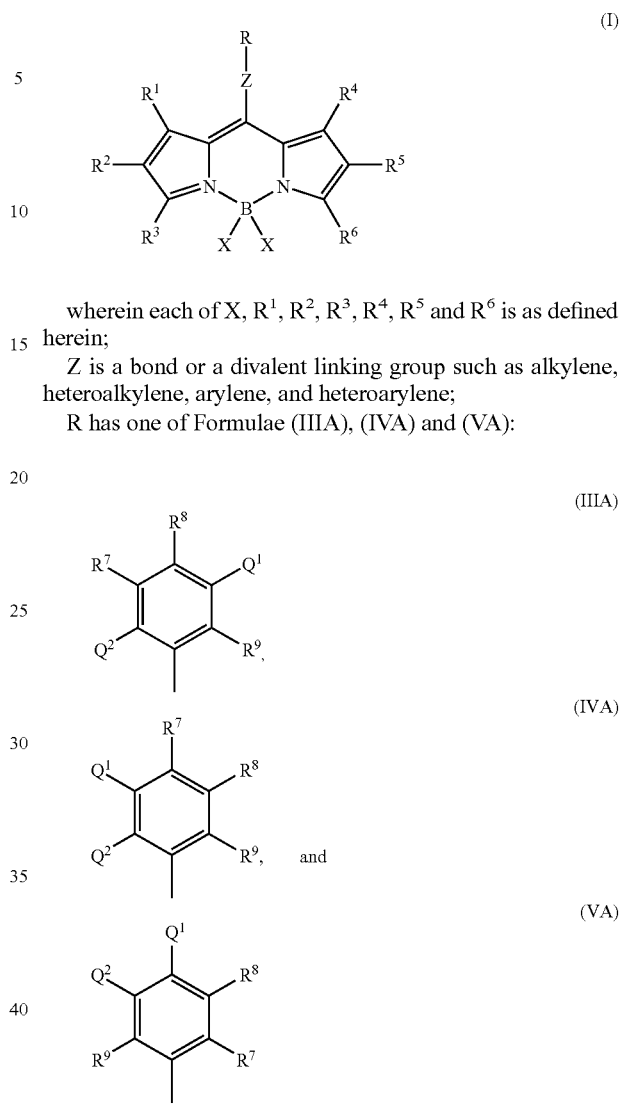

wherein each of X, $R^1$, $R^2$, $R^3$, $R^4$, $R^5$ and $R^6$ is as defined herein;

Z is a bond or a divalent linking group such as alkylene, heteroalkylene, arylene, and heteroarylene;

R has one of Formulae (IIIA), (IVA) and (VA):

wherein each of $R^7$, $R^8$ and $R^9$ is independently hydrogen, halo, alkyl, halogenated alkyl, alkenyl, alkynyl, aryl, aralkyl, alkaryl, heterocyclyl, cycloalkyl, cycloalkenyl, cycloalkynyl, hydroxy, thio, alkoxy, alkylthio, alkoxyalkyl, cyano, nitro, carboxyl, acyl, carbamate, amido, amino, alkylamino, arylamino, dialkylamino, alkylarylamino, diarylamino, or heteroalkyl, or $R^7$ and $R^8$ of Formula (IIIA), (IVA) or (VA) or $R^8$ and $R^9$ of Formula (IVA) together form a 5-, 6-, or 7-membered cycloalkyl, cycloalkenyl, aryl, heteroalkyl or heteroaryl ring; and each of $Q^1$ and $Q^2$ is an electron-donating group. In some embodiments, each of $Q^1$ and $Q^2$ is independently amino or —O-$Q^3$, where $Q^3$ is hydrogen, alkyl, alkenyl, alkoxyalkyl, cycloalkyl, cycloalkenyl, cycloalkynyl, aryl, alkaryl, aralkyl, alkylamido, alkoxyamido, alkoxycarbonyl, halogenated alkyl or heteroalkyl, with the proviso that $Q^1$ and $Q^2$ are not both amino. In further embodiments, each of $Q^1$ and $Q^2$ is —O-$Q^3$. In further embodiments, $Q^1$ is —O-$Q^3$ and $Q^2$ is amino. In further embodiments, $Q^1$ is amino and $Q^2$ is —O-$Q^3$.

In certain embodiments, R is a monovalent dioxygenated aryl group having one of Formulae (IIIB), (IVB) and (VB):

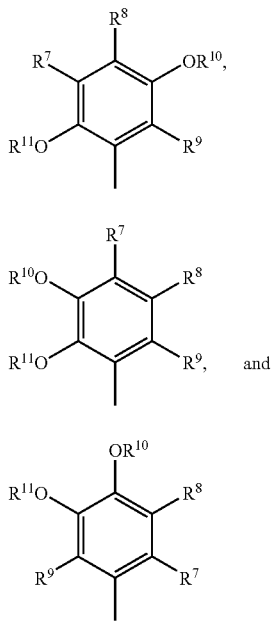

wherein each of $R^7$, $R^8$ and $R^9$ is as defined herein; and each of $R^{10}$ and $R^{11}$ is independently hydrogen or an electron-donating group.

In some embodiments, each of $R^{10}$ and $R^{11}$ is independently hydrogen, alkyl, alkenyl, alkoxyalkyl, cycloalkyl, cycloalkenyl, cycloalkynyl, aryl, alkaryl, arylalkyl, alkylamido, alkoxyamido, alkoxycarbonyl, halogenated alkyl or heteroalkyl. In other embodiments, $R^{11}$ is hydrogen. In further embodiments, $R^{10}$ is alkyl such as methyl, ethyl, propyl, isopropyl, butyl, isobutyl, tert-butyl, and the like. In further embodiments, $R^{11}$ is hydrogen and $R^{10}$ is methyl.

In other embodiments, Z is a bond. In other embodiments, Z is arylene. In further embodiments, Z is arylene having one of Formulae (a)-(p):

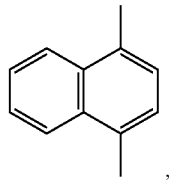

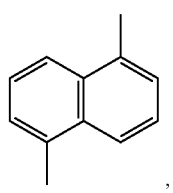

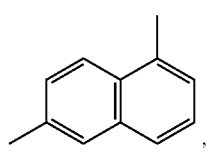

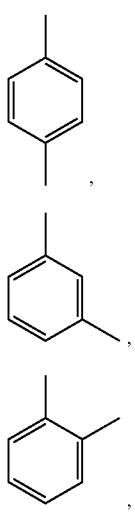

-continued

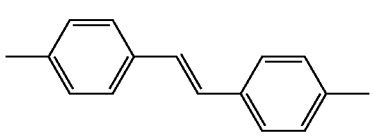

(p)

In further embodiments, one or more of Formulae (a)-(p) is optionally substituted.

In certain embodiments, the compounds or hypochlorous acid probes disclosed herein are represented by Formula (VI):

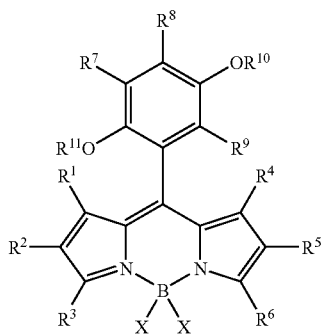

(VI)

wherein each of X, $R^1$, $R^2$, $R^3$, $R^4$, $R^5$, $R^6$, $R^7$, $R^8$, $R^9$, $R^{10}$ and $R^{11}$ is as defined herein. In some embodiments, $R^{11}$ is hydrogen. In other embodiments, $R^{10}$ is alkyl such as methyl, ethyl, propyl, isopropyl, butyl, isobutyl, tert-butyl, and the like. In further embodiments, $R^{11}$ is hydrogen; and $R^{10}$ is methyl. In certain embodiments, the two X groups are different. In other embodiments) the two X groups are the same. In further embodiments, each of the two X groups is F. In some embodiments, each of $R^1$, $R^2$, $R^4$ and $R^5$ is hydrogen; and each of $R^3$ and $R^6$ is —C(=O)—Y wherein Y is diethylamino.

In some embodiments, each of $R^3$ and $R^6$ of Formula (I) or (VI) is independently hydrogen or —C(=O)$NR^{12}R^{13}$, wherein each of $R^{12}$ and $R^{13}$ is independently hydrogen, alkyl or aryl. In further embodiments, each of $R^3$ and $R^6$ of Formula (VI) is —C(=O)$NR^{12}R^{13}$, wherein each of $R^{12}$ and $R^{13}$ is alkyl. In further embodiments, each of $R^3$ and $R^6$ is —C(=O)N(CH$_2$CH$_3$)$_2$.

In other embodiments, $R^2$ and $R^3$ of Formula (I), (II) or (VI) together form a ring. In other embodiments, the $R^2$ and $R^3$ groups together form a 5-, 6- or 7-membered cycloalkyl, cycloalkenyl, aryl, heteroalkyl or heteroaryl ring. In further embodiments, the $R^1$ and $R^3$ groups together form a benzo, naphtha, anthrax, pyrido, pyridazino, pyrimido, pyrazino, triazino, tetrazino, pyrazolo, triazolo, or pyrrolo ring. In some embodiments, the $R^2$ and $R^3$ groups together form a benzo ring.

In further embodiments, $R^5$ and $R^6$ of Formula (I), (II) or (VI) together form a ring. In other embodiments, the $R^5$ and $R^6$ groups together form a 5-, 6- or 7-membered cycloalkyl, cycloalkenyl, aryl, heteroalkyl or heteroaryl ring. In further embodiments, the $R^5$ and $R^6$ groups together form a benzo, naphtha, anthrax, pyrido, pyridazino, pyrimido, pyrazino, triazino, tetrazino, pyrazolo, triazolo, or pyrrolo ring. In some embodiments, the $R^5$ and $R^6$ groups together form a benzo ring.

In further embodiments, $R^1$ and $R^2$ of Formula (I), (II) or (VI) together form a ring. In other embodiments, the $R^1$ and $R^2$ groups together form a 5-, 6- or 7-membered cycloalkyl, cycloalkenyl, aryl, heteroalkyl or heteroaryl ring. In further embodiments, the $R^1$ and $R^2$ groups together form a benzo, naphtha, anthrax, pyrido, pyridazino, pyrimido, pyrazino, triazino, tetrazino, pyrazolo, triazolo, or pyrrolo ring. In some embodiments, the $R^1$ and $R^2$ groups together form a benzo ring.

In further embodiments, $R^4$ and $R^5$ of Formula (I), (II) or (VI) together form a ring. In other embodiments, the $R^4$ and $R^5$ groups together form a 5-, 6- or 7-membered cycloalkyl, cycloalkenyl, aryl, heteroalkyl or heteroaryl ring. In further embodiments, the $R^4$ and $R^5$ groups together form a benzo, naphtha, anthrax, pyrido, pyridazino, pyrimido, pyrazino, triazino, tetrazino, pyrazolo, triazolo, or pyrrolo ring. In some embodiments, the $R^4$ and $R^5$ groups together form a benzo ring.

In further embodiments, $R^7$ and $R^8$ of Formula (VI) together form a ring. In other embodiments, the $R^7$ and $R^8$ groups together form a 5-, 6- or 7-membered cycloalkyl, cycloalkenyl, aryl, heteroalkyl or heteroaryl ring. In further embodiments, the $R^7$ and $R^8$ groups together form a benzo, naphtha, anthrax, pyrido, pyridazino, pyrimido, pyrazino, triazino, tetrazino, pyrazolo, triazolo, or pyrrolo ring. In some embodiments, the $R^7$ and $R^8$ groups together form a benzo ring.

In certain embodiments, the compounds or hypochlorous acid probes disclosed herein are represented by Formula (VII) or (VIII):

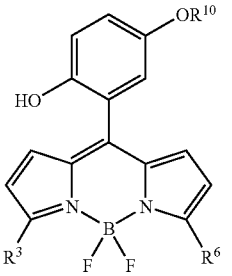

(VII)

or

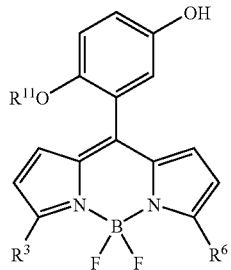

(VIII)

wherein $R^{10}$ is alkyl; $R^{11}$ is alkyl; and each of $R^3$ and $R^6$ is independently hydrogen or —C(=O)—Y, wherein Y is hydrogen, alkoxy, hydroxy, thio, alkyl, alkenyl, alkynyl, cycloalkyl, cycloalkenyl, cycloalkynyl, aryl, alkaryl, arylalkyl, amino, alkylamino, arylamino, dialkylamino, alkylarylamino, diarylamino, alkylthio, or 3- to 7-membered heterocyclyl ring. In some embodiments, each of $R^3$ and $R^6$ is —C(=O)$NR^{12}R^{13}$ wherein each of $R^{12}$ and $R^{13}$ is alkyl. In further embodiments, each of $R^3$ and $R^6$ is —C(=O)N(CH$_2$CH$_3$)$_2$.

In some embodiments, the hypochlorous acid probe disclosed herein is Compound (5) or (6), or an isomer thereof:

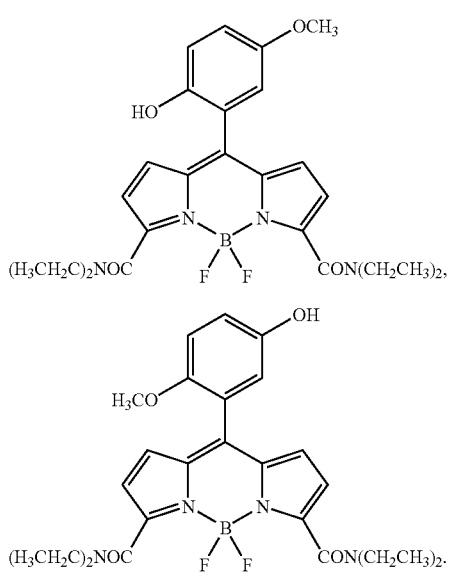

(5)

or (6)

Also provided herein are reagent compositions for measuring directly or indirectly hypochlorous acid or hypochlorite in chemical or biological samples such as microorganism, or a cell or tissue from animals. The reagent composition comprises the hypochlorous acid probe disclosed herein. In some embodiments, the reagent composition further comprises a solvent, an acid, a base, a buffer solution or a combination thereof a base, a buffer solution or a combination thereof.

Also provided herein are methods for measuring directly or indirectly hypochlorous acid or hypochlorite in a sample. In some embodiments, the methods comprise the steps of (a) contacting a hypochlorous acid probe disclosed herein with the sample to form a fluorescent compound; and (b) measuring fluorescence properties of the fluorescent compound. In some embodiments, the fluorescence properties are measured with methods disclosed herein or any method known to a person skilled in the art. In other embodiments, the sample is a chemical sample or biological sample. In further embodiments, the sample is a biological sample comprising a microorganism, or a cell or tissue from animals.

Also provided herein are high-throughput screening fluorescent methods for detecting directly or indirectly hypochlorous acid or hypochlorite in samples. In some embodiments, the high-throughput screening fluorescent methods comprise the steps of (a) contacting a hypochlorous acid probe disclosed herein with the samples to form one or more fluorescent compounds; and (b) measuring fluorescence properties of the fluorescent compounds. In other embodiments, the fluorescence properties are measured with methods disclosed herein or any method known to a person skilled in the art.

Also provided herein are high-throughput methods for screening one or more target compounds that can directly or indirectly increase or decrease the level of hypochlorous acid or hypochlorite. In some embodiments, the high-throughput methods comprise the steps of (a) contacting a hypochlorous acid probe disclosed herein with the target compounds to form one or more fluorescent compounds; and (b) measuring fluorescence properties of the fluorescent compounds to determine the target compounds quantitatively or qualitatively. In other embodiments, the fluorescence properties are measured with methods disclosed herein or any method known to a person skilled in the art.

In some embodiments, informaties systems can be used and implemented in the high-throughput methods disclosed herein. In other embodiments, the informatics systems provide the software control of the physical devices used in the high-throughput method. In other embodiments, the informatics systems organize electronic data generated by the high-throughput methods. In further embodiments, the informatics systems store electronic data generated by the high-throughput methods.

General Synthetic Procedures

The compounds or hypochlorous acid probes disclosed herein may be made by one skilled in the art with known organic syntheses as well as various general or specific synthetic procedures disclosed herein. For example, the hypochlorous acid probes of Formula (I) can be synthesized by the following general procedure as shown in Scheme (B) below.

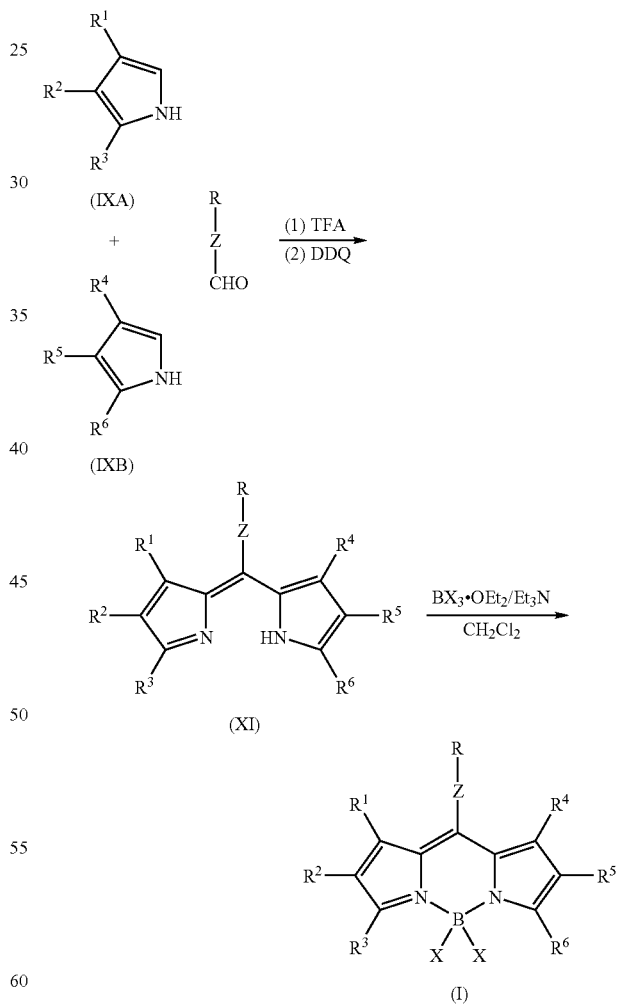

Each of R, X, $R^1$, $R^2$, $R^3$, $R^4$, $R^5$ and $R^6$ in Scheme (B) is as defined above. The pyrroles of Formula (IXA) and (IXB) can react with the aldehyde of Formula (X) in the presence of an acid catalyst in an appropriate solvent such as dichloromethane or 1,2-dichloroethane at temperature ranging from room temperature to 80° C. After a substantial amount of the aldehyde of Formula (X) reacts with the pyrroles of Formula (IXA) and (IXB), an oxidizing agent, such as benzoquinones, can be added to the reaction mixture to form the dipyrrole of Formula (XI). Some non-limiting examples of suitable benzoquinones include 2,3-dichloro-5,6-dicyano-1,4-benzoquinone (DDQ) and 2,3,5,6-tetrachloro-parabenzoquinone. The dipyrrole of Formula (XI) can be purified by conventional techniques such as washing, filtration, extraction, evaporation, distillation, recrystallization, chromatography and the like.

Some non-limiting examples of suitable acid catalyst include trifluoroacetic acid (TFA), 4-(trifluoromethyl)benzoic acid, p-toluenesulfonic acid, methanesulfonic acid, acetic anhydride, Lewis acids (e.g., $Et_2AlCl$, $EtAlCl_2$, $BF_3$, $SnCl_4$, $AlCl_3$, Ti (isopropoxide)$_4$ and $TiCl_4$) and combinations thereof. In some embodiments, the acid catalyst is trifluoroacetic acid.

In some embodiments, the pyrrole of Formula (IXA) is the same as the pyrrole of Formula (IXB). In other embodiments, the pyrrole of Formula (IXA) and the pyrrole of Formula (IXB) are different. The pyrroles of Formula (IXA) and (IXB) can be purchased from a commercial supplier such as Aldrich Chemical or prepared by known methods. The chemistry and preparations of pyrroles are disclosed in Richard Alan Jones et al., "*Chemistry of Pyrroles*," Academic Press (1977), which is incorporated herein by reference.

The aldehyde of Formula (X) can be purchased from a commercial supplier such as Aldrich Chemical or prepared by methods known to a skilled artisan. For example, the aldehyde of Formula (X) can be prepared by formylating an aryl compound having formula R—Z—H where R and Z are as defined above. In some embodiments, the aldehyde of Formula (X) can be prepared by formylating an aryl compound having one of Formulae (IIID), (IVD) and (VD):

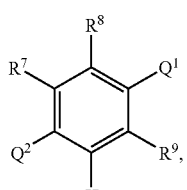

(IIID)

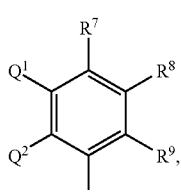

(IVD)

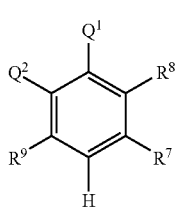

(VD)

wherein each of $R^7$, $R^8$, $R^9$, $Q^1$ and $Q^2$ is as defined herein.

In certain embodiments, the aldehyde of Formula (X) can be prepared by formylating an aryl compound having one of one of Formulae (IIIE), (IVE) and (VE):

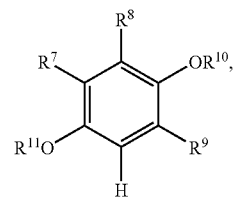

(IIIE)

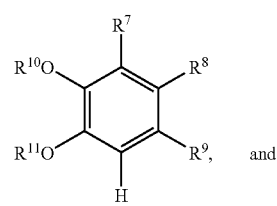

(IVE)

and

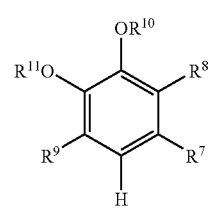

(VE)

wherein each of $R^7$, $R^8$, $R^9$, $R^{10}$ and $R^{11}$ is as defined herein.

When R is or comprises a phenolic group, the formylation can be carried out with paraformaldehyde alone. Alternatively, when Z is an arylene group, the formylation can be carried out with a mixture of dimethylformamide and phosphorus oxychloride via the Vilsmeier-Haack reaction. Similarly, when Z is a bond and R is a dioxygenated aryl group, the aldehyde of Formula (X) can be prepared by formylating a dioxygenated aryl compound having formula R—H. Alternatively, Reimer-Tiemann reaction, Duff reaction, Gattermann-Koch reaction, and Gattermann reaction can be used to prepare the aldehyde of Formula (X) with the appropriate starting materials.

Next, the dipyrrole of Formula (XI) can be treated with boron trihalide etherate and triethylamine in a suitable solvent, such as dichloromethane, to form the hypochlorous acid probe of Formula (I). In some embodiments, the boron trihalide is $BF_3$, $BCl_3$, $BBr_3$ or a combination thereof. The hypochlorous acid probe of Formula (I) can be purified by conventional techniques such as washing, filtration, extraction, evaporation, distillation, recrystallization, chromatography and the like.

Similarly, the compounds or hypochlorous acid probe of Formula (VI) can be synthesized by the following general procedure as shown in Scheme (C) below.

Scheme (C)

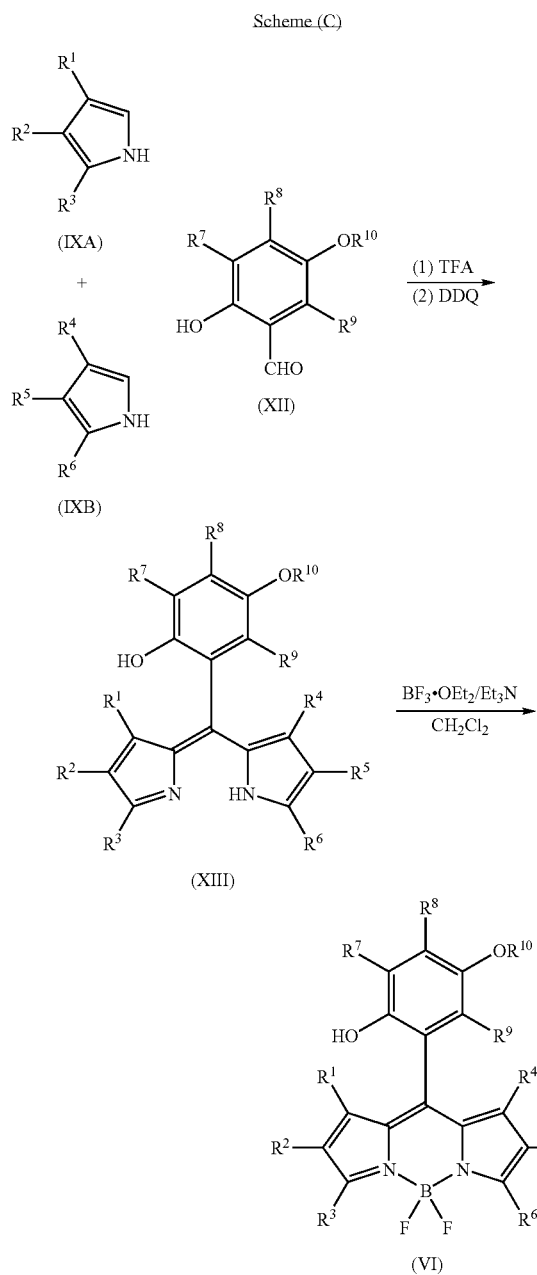

Each of R, X, $R^1$, $R^2$, $R^3$, $R^4$, $R^5$, $R^6$, $R^7$, $R^8$, $R^9$ and $R^{10}$ in Scheme (C) is as defined herein. The pyrroles of Formula (IXA) and (IXB) can react with the aldehyde of Formula (XII) in the presence of an acid catalyst, as disclosed in Scheme (B) above, in an appropriate solvent such as dichloromethane or 1,2-dichloroethane at a temperature ranging from room temperature to 80° C. In some embodiments, the pyrrole of Formula (IXA) is the same as the pyrrole of Formula (IXB). In other embodiments, the pyrrole of Formula (IXA) and the pyrrole of Formula (IXB) are different.

The aldehyde of Formula (XII) can be purchased from a commercial supplier such as Aldrich Chemical or prepared by methods known to a skilled artisan. For example, the aldehyde of Formula (XII) can be prepared by formylating an aryl compound having formula (XIV):

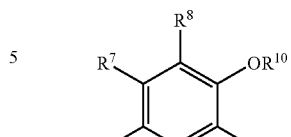

wherein each of $R^7$, $R^8$, $R^9$ and $R^{10}$ is as defined herein. The formylation of the aryl compound of Formula (XIV) can be carried out with paraformaldehyde alone. Alternatively the formylation can be carried out with a mixture of dimethylformamide and phosphorus oxychloride via the Vilsmeier-Haack reaction.

After the aldehyde of Formula (XIV) reacts completely, an oxidizing agent, such as benzoquinones, can be added to the reaction mixture to form the dipyrrole of Formula (XIII). The dipyrrole of Formula (XIII) can be purified by conventional techniques such as washing, filtration, extraction, evaporation, distillation, recrystallization, chromatography and the like.

Next, the dipyrrole of Formula (XIII) can be treated with boron trihalide etherate and triethylamine, as disclosed in Scheme (B) above, in a suitable solvent, such as dichloromethane, to form the hypochlorous acid probe of Formula (VI). The hypochlorous acid probe of Formula (VI) can be purified by conventional techniques such as washing, filtration, extraction, evaporation, distillation, recrystallization, chromatography and the like.

Some functional groups of the formulae in Schemes B and C can be protected by protecting groups. In some embodiments, the Schemes B and C may be optimized by using different protecting groups. The chemistry of protecting groups can be found in the literature such as Greene, T. W. and Wuts, P. G. M., *Protective Groups in Organic Synthesis,* 3rd ed., John Wiley & Sons, Inc., 1999, which is incorporated herein by reference.

EXAMPLES

The following Examples 1-4 are detailed descriptions of the methods of making and using some hypochlorous acid probes represented by general Formulae (I), (VI), (VII) and (VIII). The detailed disclosure falls within the scope of, and serve to exemplify, the above described General Synthetic Procedures which form part of this disclosure. These examples are presented for illustrative purposes only and are not intended to limit the scope of this disclosure.

Example 1

Synthetic Schemes for Compound 5

Synthesis of pyrrole-2-carboxylic Acid

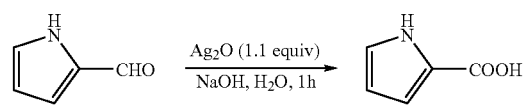

Pyrrole-2-carboxaldehyde (10.0 g, 105 mmol) was dissolved in 50 mL of methanol and then diluted by 500 mL of distilled water. Fresh silver oxide (48.3 g, 210 mmol) and sodium hydroxide (8.5 g, 212 mmol) were added to the pyrrole-2-carboxaldehyde solution. After the reaction mixture was stirred for 1 hour at room temperature, the precipitate was filtered off and washed with hot water. The combined filtrates and washings were extracted with diethyl ether (500 mL) and then acidified at 0° C. with 37% hydrochloric acid. The solution was extracted with diethyl ether (200 mL×4). The combined organic extract was dried over magnesium sulfate. The solvent was evaporated under reduced pressure to yield 9.9 g of pyrrole-2-carboxylic acid (85% yield).

Synthesis of Compound 1

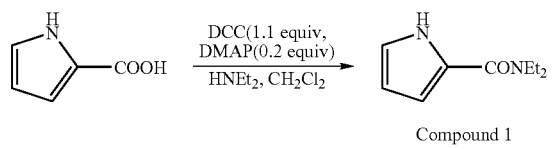

Compound 1

Pyrrole-2-carboxylic acid (10.0 g, 90 mmol) was dissolved in 250 mL of dichloromethane. N,N'-Dicyclohexylcarbodiimide (DCC) (20.4 g, 99 mmol), 4-dimethyl-aminopyridine (DMAP) (2.2 g, 18 mmol) and diethylamine (10.2 mL, 99 mmol) were added subsequently at 0° C. under an Argon atmosphere. The reaction mixture was stirred at 0° C. for 30 minutes then stirred at room temperature for 8 hours. After the solution was diluted with dichloromethane and the solid was filtered off, the filtrate was washed by diluted hydrochloric acid, followed by saturated sodium bicarbonate solution. The organic layer was dried over $Na_2SO_4$ and then the solvent was evaporated under reduced pressure. The residue was purified by column chromatography using 35% EtOAc in n-hexane as diluent to obtain 10.5 g of Compound 1 as a white solid (70% yield).

Synthesis of 2-hydroxy-5-methoxybenzaldehyde

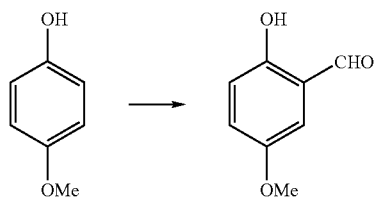

To a mixture of compound p-methoxyphenol (3 g, 24.2 mmol), anhydrous magnesium dichloride (3.48 g, 37.0 mmol) and dry triethylamine (12.8 mL, 92.1 mmol) in 100 mL of acetonitrile was added dry paraformaldehyde (5 g, 167 mmol). The reaction mixture was refluxed for 8 hours and cooled down to room temperature. Then the reaction mixture was poured into 5% HCl (300 mL) and extracted with diethyl ether (200 mL) for three times. The combined organic layers were dried over anhydrous $Na_2SO_4$, filtered, and evaporated. The residue was purified by flash column chromatography (20% EtOAc in n-hexane) to yield 3.35 g of 2-hydroxy-5-methoxybenzaldehyde (91% yield).

Synthesis of Compound 2

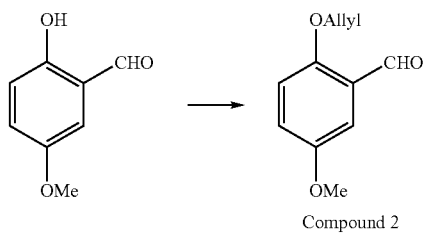

Compound 2

To a solution of 2-hydroxy-5-methoxybenzaldehyde (3.3 g, 21.7 mmol) in 60 mL of THF were added allyl bromide (3.2 mL, 32.7 mmol) and $K_2CO_3$ (12 g, 86.2 mmol). The reaction mixture was refluxed for 10 hours. Then the mixture was washed with 20 mL of water for two times. The combined organic extracts were dried over $Na_2SO_4$, filtered, and evaporated. The crude compound was purified by column chromatography (20% EtOAc in n-hexane) to yield 3.33 g of Compound 2 as colorless oil (80% yield). Compound 2 was characterized by the following physical properties: $^1H$ NMR (400 MHz, $CDCl_3$): δ 10.48 (s, 1H), 7.30 (d, J=3.3 Hz, 1H), 7.11 (dd, J=9.0, 3.3 Hz, 1H), 6.92 (d, J=9.0 Hz, 1H), 6.08-6.02 (m, 1H), 5.42 (dd, J=17.2, 1.4 Hz, 1H), 5.31 (dd, J=10.6, 1.2 Hz, 1H), 4.60-4.59 (m, 2H), 3.79 (s, 3H); $^{13}C$ NMR (100 MHz, $CDCl_3$): δ 189.2, 155.5, 153.6, 132.5, 125.2, 123.2, 117.8, 114.7, 110.1, 69.7, 55.6; IR ($CH_2Cl_2$) 2996, 1704, 1638 $cm^{-1}$; LRMS (EI) m/z (%) 192 ($M^+$; 63), 151 (100); HRMS (EI): calcd for $C_{11}H_{12}O_3$: 192.0786, Found: 192.0781.

Synthesis of Compound 3

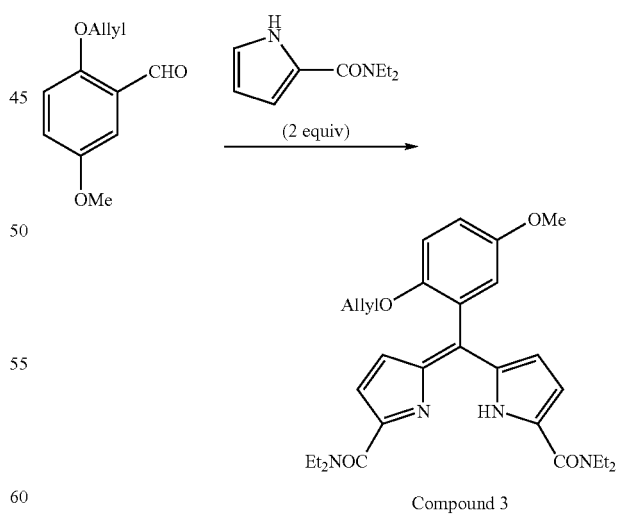

Compound 3

Compound 1 (4.2 g, 25.4 mmol) and Compound 2 (2.44 g, 12.7 mmol) were dissolved in 20 mL of anhydrous 1,2-dichloroethane under Argon atmosphere. One drop of trifluoroacetic acid (TFA) was added, and the solution was heated under reflux. After TLC monitoring (silica; $CH_2Cl_2$) showed complete consumption of Compound 2, a solution of DDQ (2,3-dichloro-5,6-dicyano-1,4-benzoquinone) (2.89 g, 12.7 mmol) in 40 mL of $CH_2Cl_2$ was added, and stirring was continued for 20 minutes. The reaction mixture was washed with water, dried over $MgSO_4$, filtered, and evaporated. The crude compound was purified by column chromatography (40% EtOAc, 20% $CH_2Cl_2$ in n-hexane) to yield Compound 3 as a brown-red oil (1.51 g, 62% yield). Compound 3 was characterized by the following physical properties: $^1H$ NMR (400 MHz, $CDCl_3$): δ 12.2 (br, 1H), 6.93 (d, J=2.6 Hz, 2H), 6.84 (d, J=2.4 Hz, 1H), 6.64 (d, J=4.3 Hz, 2H), 6.52 (d, J=4.3 Hz, 2H), 5.79-5.72 (m, 1H), 5.14-5.06 (m, 2H), 4.42-4.40 (m, 2H), 3.78 (s, 3H), 3.62 (br, 8H), 1.23 (m, 12H); $^{13}C$ NMR (100 MHz, $CDCl_3$): δ 163.0, 153.0, 150.5, 149.0, 142.0, 139.0, 133.2, 128.2, 127.1, 119.4, 117.3, 116.9, 115.2, 114.6, 70.2, 55.7, 43.0 (br), 14.0 (br); IR ($CH_2Cl_2$) 2944, 1658, 1635 $cm^{-1}$; LRMS (EI) m/z (%) 504 ($M^+$; 19), 447 (100); HRMS (EI): calcd for $C_{29}H_{36}N_4O_4$: 504.2737, Found: 504.2726.

Synthesis of Compound 4

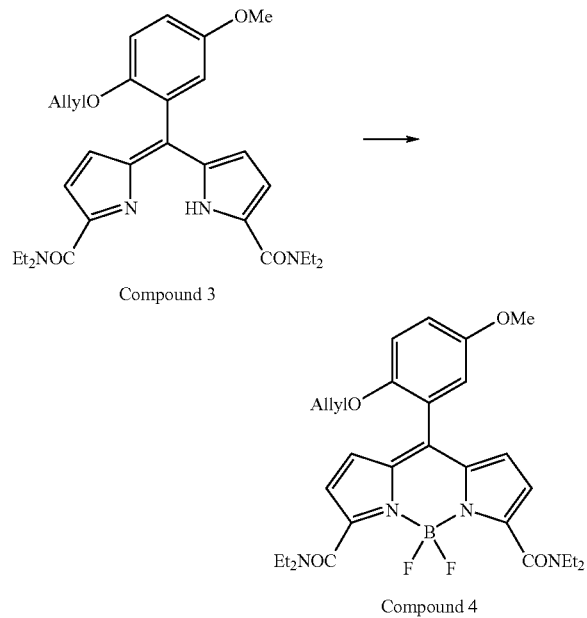

Compound 3

Compound 3 (2.2 g, 4.38 mmol) and triethylamine (12.3 mL, 87.5 mmol) were dissolved in 137 mL of absolute dichloromethane under an Argon atmosphere, and the solution was stirred at room temperature for 10 minutes. $BF_3.OEt_2$ (12.3 mL, 96.3 mmol) was added, and stirring was continued for 4 hours. The reaction mixture was washed with water and 2N NaOH. The aqueous solution was extracted with $CH_2Cl_2$. The combined organic extracts were dried over $Na_2SO_4$, filtered, and evaporated. The crude compound was purified by column chromatography (40% EtOAc, 20% $CH_2Cl_2$ in n-hexane) to yield Compound 4 as a solid (1.47 g, 61% yield). Compound 3 was characterized by the following physical properties: m.p. 72.0-73.9° C.; $^1H$ NMR (300 MHz, $CDCl_3$): δ 7.01-6.99 (m, 2H), 6.87 (d, J=2.5 Hz, 1H), 6.84 (d, J=4.2 Hz, 2H), 6.44 (d, J=4.2 Hz, 2H), 5.84-5.76 (m, 1H), 5.16 (dd, J=17.1, 1.5 Hz, 1H), 5.11 (dd, J=10.3, 1.4 Hz, 1H), 4.45 (dd, J=3.4, 1.5 Hz, 2H), 3.79 (s, 3H), 3.57 (q, J=7.1 Hz, 4H), 3.29 (q, J=7.1 Hz, 4H), 1.26 (t, J=7.1 Hz, 6H), 1.09 (t, J=7.1 Hz, 6H); $^{13}C$ NMR (75 MHz, $CDCl_3$): δ 162.6, 153.0, 151.2, 149.8, 144.6, 135.1, 132.5, 131.2, 123.2, 117.0, 116.6, 116.4, 114.4, 69.6, 55.6, 42.8, 38.5, 13.8, 11.9; $^{19}F$ NMR (376.5 MHz, $CDCl_3$): δ −144.1 (m, J=30.1 Hz), −145.5 (m, J=30.1 Hz); IR ($CH_2Cl_2$) 2980, 1734, 1640 $cm^{-1}$; LRMS (EI) m/z (%) 552 ($M^+$; 16), 495 (100); HRMS (EI): calcd for $C_{29}H_{35}BF_2N_4O_4$: 552.2719, Found: 552.2715.

Synthesis of Compound 5

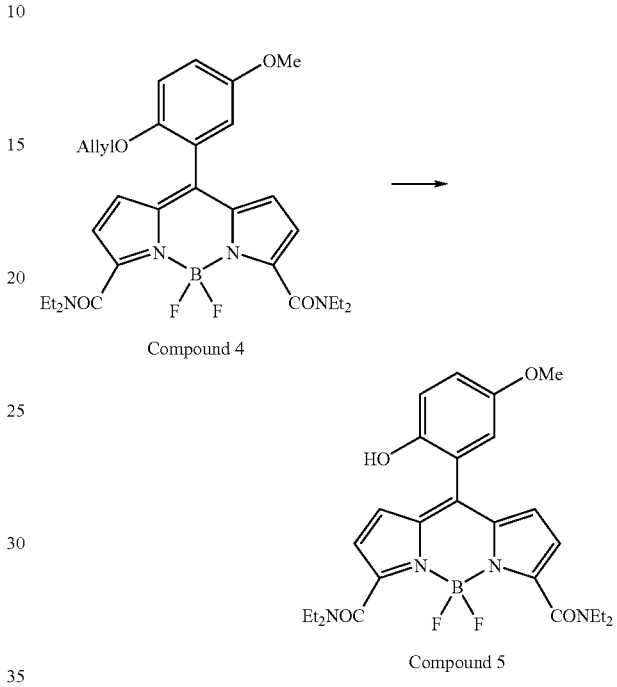

To a solution of Compound 4 (400 mg, 0.725 mmol) in 50 mL of ethanol was bubbled by Argon gas to remove any dissolved oxygen for 30 min. Then $Pd(PPh_3)_4$ (83.7 mg, 0.0725 mmol) was added slowly under strong argon stream. The reaction mixture was refluxed for 6 hours. The solid was filtered off and the filtrates were dried over $MgSO_4$. The solvent was evaporated under reduced pressure. The residue was purified by column chromatography (5% MeOH in $CHCl_3$) to yield Compound 5 as a solid (258 mg, 70% yield). Compound 5 was characterized by the following physical properties: m.p. 89.6-91.2° C.; $^1H$ NMR (400 MHz, $CDCl_3$): δ 8.40 (br, 1H), 7.0 (d, J=8.9 Hz, 1H), 6.90-6.85 (m, 3H), 6.72 (d, J=3.1 Hz, 1H), 6.37 (d, J=4.2 Hz, 2H), 3.71 (s, 3H), 3.54 (br, 4H), 3.24 (q, J=7.3 Hz, 4H), 1.26 (t, J=7.1 Hz, 6H), 1.06 (t, J=7.1 Hz, 6H); $^{13}C$ NMR (100 MHz, $CDCl_3$): δ 163, 151.9, 150.3, 148.7, 146.0, 135.2, 131.9, 120.3, 117.9, 117.4, 116.6, 116.3, 55.7, 43.1, 38.7, 13.9, 12.0; $^{19}F$ NMR (376.5 MHz, $CDCl_3$): −143.4 (m, J=30.1 Hz), −145.3 (m, J=30.1 Hz); IR ($CH_2Cl_2$) 3234, 1654, 1573 $cm^{-1}$; LRMS (EI) m/z (%) 512 ($M^+$; 18), 277 (100); HRMS (EI): calcd for $C_{26}H_{31}BF_2N_4O_4$: 512.2406, Found: 512.2405.

Example 2

Detection of Hypochlorous Acid with Compound 5

UV-Visible Absorption Spectrum of Compound 5

Compound 5 obtained in Example 1 was dissolved in dichloromethane to form a 10 mM solution. The absorption spectrum of the 10 mM solution of Compound 5 was measured and shown in FIG. 1. The data in FIG. 1 show that Compound 5 has an absorption maximum at about 520 nm Emission Spectra of Compound 5

Figure 2:
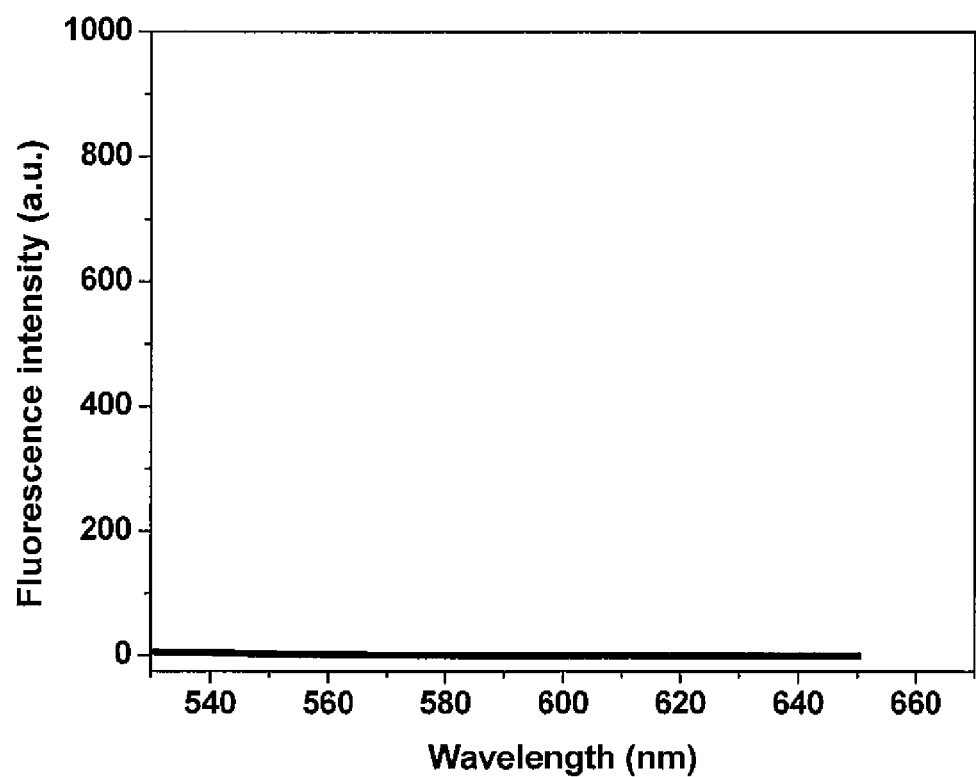
FIG. 2 depicts a fluorescence spectrum of a 10 μM solution of Compound 5 in 0.1 M potassium phosphate buffer (pH 7.4). The fluorescence intensity was determined with an excitation at 520 nm.

Compound 5 obtained in Example 1 was dissolved in DMF to a concentration of 10 mM, and then the solution was diluted to 10 µM by 0.1 M potassium phosphate buffer (pH 7.4). The fluorescence spectrum of the 10 µM solution of Compound 5 was measured using a Hitachi F2500 fluorescence spectrometer and the photomultiplier voltage was 700 V. The slit width was 2.5 nm for both excitation and emission. The measurement was carried out at an excitation wavelength of 520 nm. The results are shown in FIG. 2 which shows that Compound 5 itself is non-fluorescent.

Detection of Hypochlorous Acid with Compound 5

Figure 3:
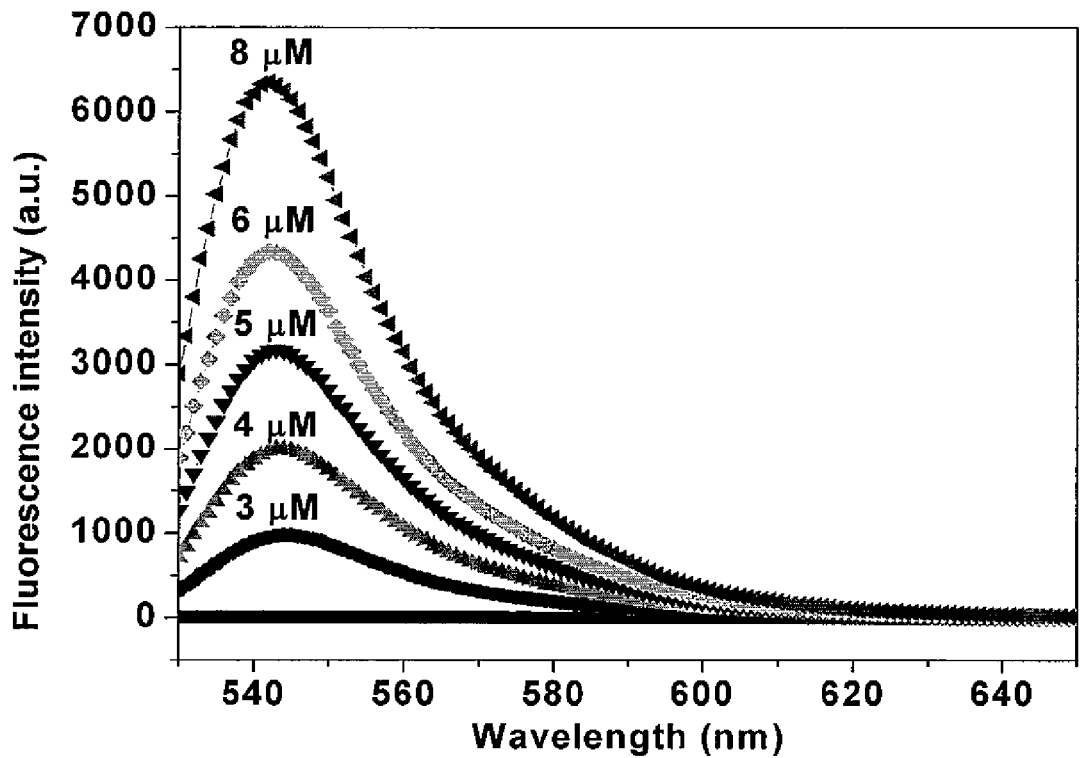
FIG. 3 depicts fluorescence spectra of a 10 μM solution of Compound 5 in 0.1 M potassium phosphate buffer (pH 7.4) taken 2 minutes after its reaction with various amounts of hypochlorite ranging from 0 to 5 equivalences. The overall volume change was less than 1% for all solutions. The fluorescence intensity was determined with an excitation at 520 nm.
Figure 4:
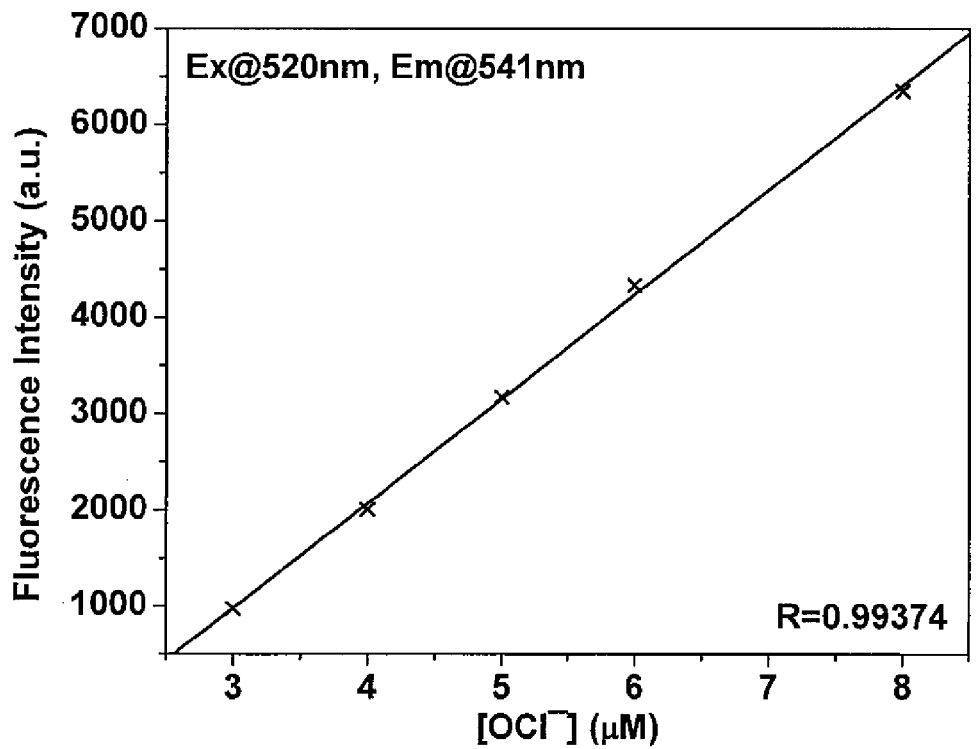
FIG. 4 depicts the linear relationship between fluorescence intensity of a 10 μM solution of Compound 5 and the concentration of hypochlorite. The fluorescence intensity was determined at 541 nm with an excitation at 520 nm.

Compound 5 obtained in Example 1 was dissolved in DMF to a concentration of 10 mM, and then the solution was diluted to 10 µM by 0.1 M potassium phosphate buffer (pH 7.4). Commercial bleach was the source of NaOCl. The concentration of NaOCl was determined by titration with sodium thiosulfate solution which was standardized by the titration with $KIO_3$. Then NaOCl was added to provide final concentrations of 0, 3, 4, 5, 6 and 8 µM. Fluorescence spectra of the solutions were measured after 2 minutes under the same conditions as mentioned above. The fluorescence spectra are shown in FIG. 3. As clearly shown in FIG. 3, the fluorescence intensity of Compound 5 increase significantly after the addition of hypochlorite. Further, FIG. 4 shows that the fluorescence intensity at 541 nm increases linear with increasing concentration of hypochlorite.

Example 3

Figure 5:
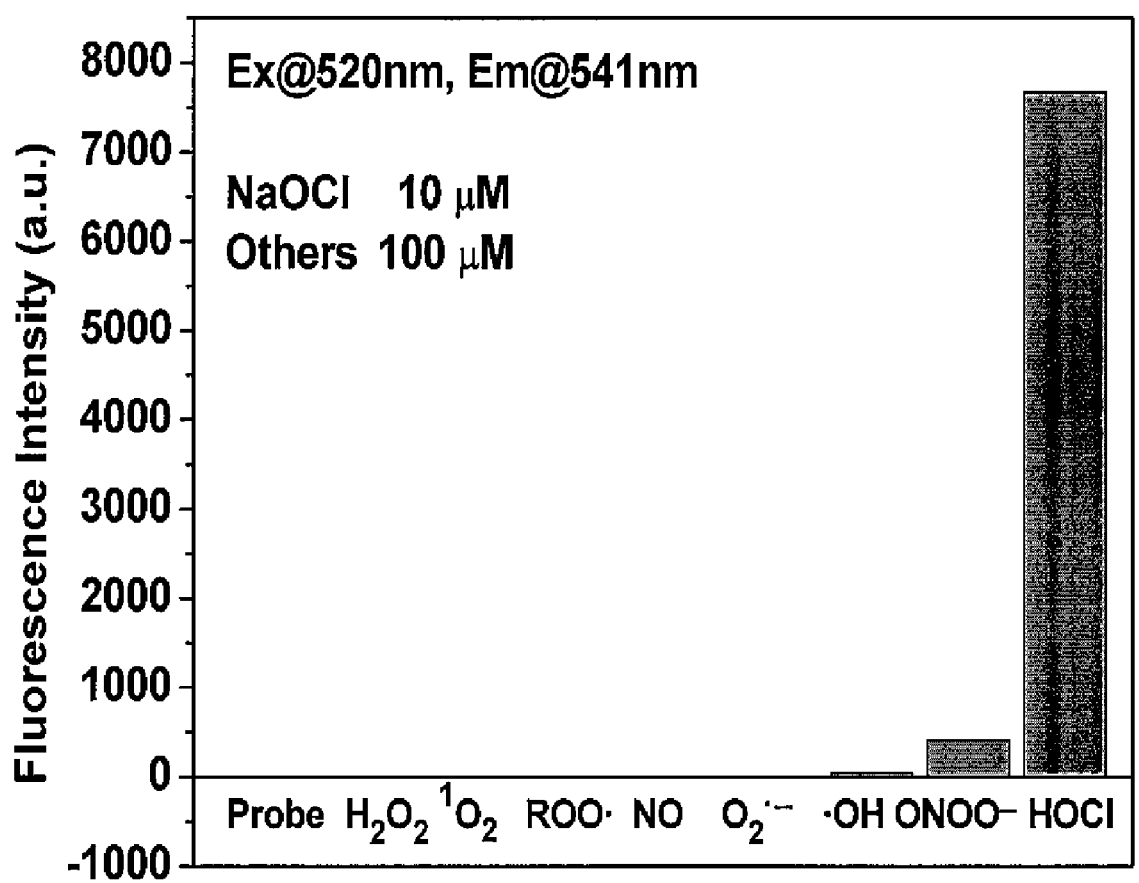
FIG. 5 depicts fluorescence intensity of a 10 μM solution of Compound 5 in various reactive oxygen species (ROS) and reactive nitrogen species (RNS) generating system. The overall volume change was less than 1% for all solutions. The fluorescence intensity was determined at 541 nm with excitation at 520 nm.

Comparison of Specificity of Compound 5 with Different Reactive Oxygen Species and Reactive Nitrogen Species The reactivity of Compound 5 was compared toward different reactive oxygen species (ROS) and reactive nitrogen species (RNS), including $OCl^-$, $H_2O_2$, $^1O_2$, NO, $O_2.^-$, .OH, $ONOO^-$ and alkylperoxyl radical (ROO.). Different reactive oxygen species and reactive nitrogen species were added independently to 5 mL of the corresponding solution of Compound 5 (10 µM in 0.1 M potassium phosphate buffer). The changes in fluorescence intensity before and after the treatment were measured. The results are shown in FIG. 5. The samples (a)-(h) in FIG. 5 were prepared as follows.
  a. $H_2O_2$ (final 100 µM) was added and then stirred for 1 hour at 25° C.
  b. (3-(1,4-Dihydro-1,4-epidioxy-1-naphthyl)propionic acid) (final 100 µM) was added and then stirred at 25° C. for 1 hour.
  c. 2,2'-Azobis(2-amidinopropane)dihydrochloride (final 100 µM) was added and then stirred at 25° C. for 1 hour.
  d. SNP (Sodium Nitroferricyanide (III) Dihydrate) (final 100 µM) was added and then stirred for 1 hour at 25° C.
  e. $O_2^-$ was generated by xanthine and xanthine oxidase. Xanthine oxidase was added firstly. After xanthine oxidase was dissolved, xanthine (final 100 µM) was added and the mixtures were stirred at 25° C. for 1 hour.
  f. Ferrous chloride (final 10 µM) was added in the presence of 10 equivalences of $H_2O_2$ (100 µM).
  g. $ONOO^-$ (final 10 µM) was added at 25° C.
  h. NaOCl (final 10 µM) was added at 25° C.

FIG. 5 shows fluorescence augmentation only upon reaction with hypochlorite. These results demonstrated that Compound 5 has a much higher reactivity towards hypochlorite among ROS and RNS in an abiotic system. Further, similar reactions do not proceed between the phenol derivative of Compound 5 and other reactive oxygen species or reactive nitrogen species present in the biological systems.

Example 4

Detection of Hypochlorous Acid with Compound 5 at Different pH Value

Figure 6:
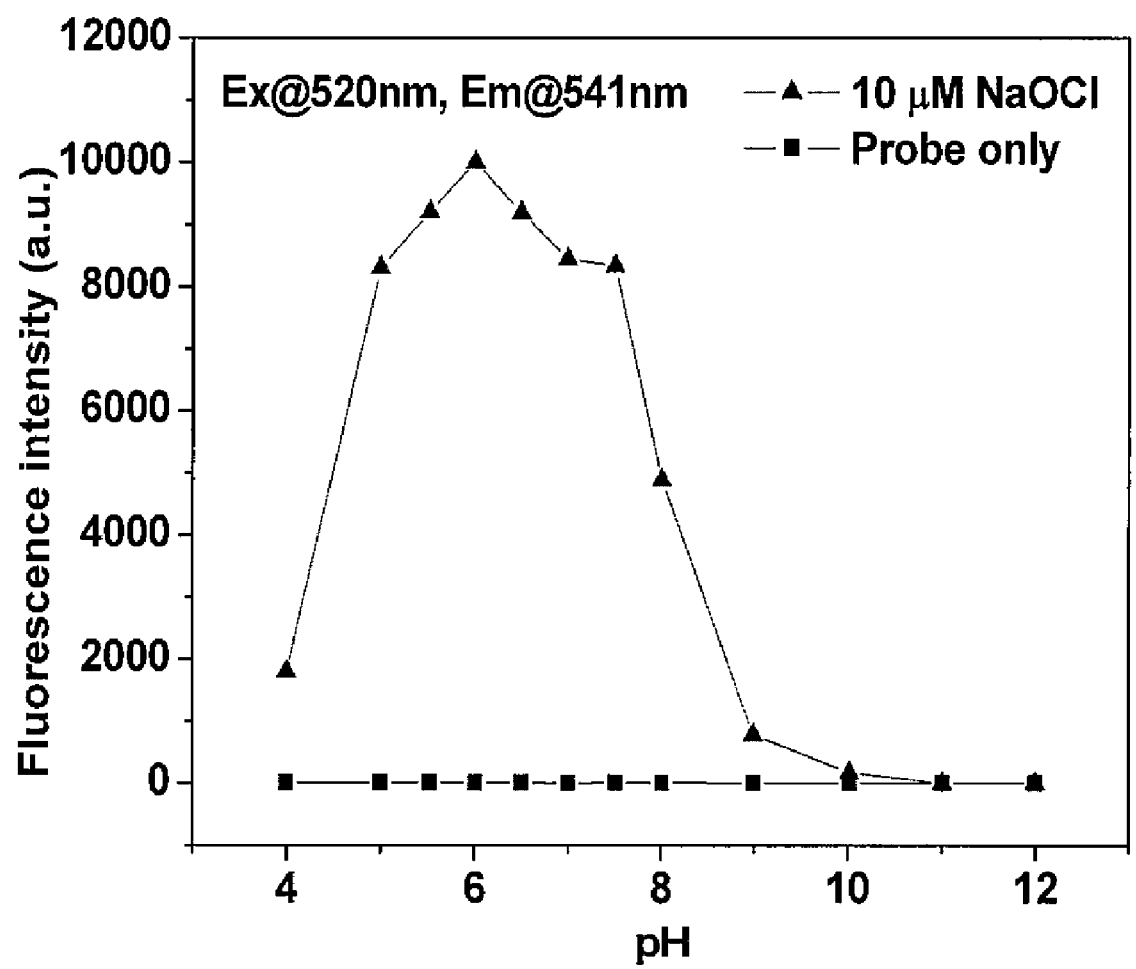
FIG. 6 depicts fluorescence spectra of a 10 μM solution of Compound 5 in 0.1 M potassium phosphate buffer taken 2 minutes after its reaction with 10 μM hypochlorite at different pH value. The overall volume change was less than 1% for all solutions. The fluorescence intensity was determined with an excitation at 520 nm.

Compound 5 obtained in Example 1 was dissolved in DMF to a concentration of 10 mM, and then the solution was diluted to 10 µM by 0.1 M potassium phosphate buffer with various pH values (from about 4.0 to about 12.0). Commercial bleach was the source of NaOCl. The concentration of NaOCl was determined by titration with sodium thiosulfate solution which was standardized by the titration with $KIO_3$. Then NaOCl was added to provide a final concentration of 10 µM. Fluorescence spectra of the solutions were measured after 2 minutes under the same conditions as mentioned above. The fluorescence spectra are shown in FIG. 6. As clearly shown in FIG. 6, the fluorescence intensity of Compound 5 is significantly higher at a pH range from about 5 to about 7.5 than at other pH values. In view of the $pK_a$ of hypochlorous acid being 7.6, it is likely that compound 5 generally detects hypochlorous acid rather than hypochlorite.

Example 5

Detection of Hypochlorous Acid with Compound 5 in $MPO/H_2O_2/Cl$-System

Figure 7:
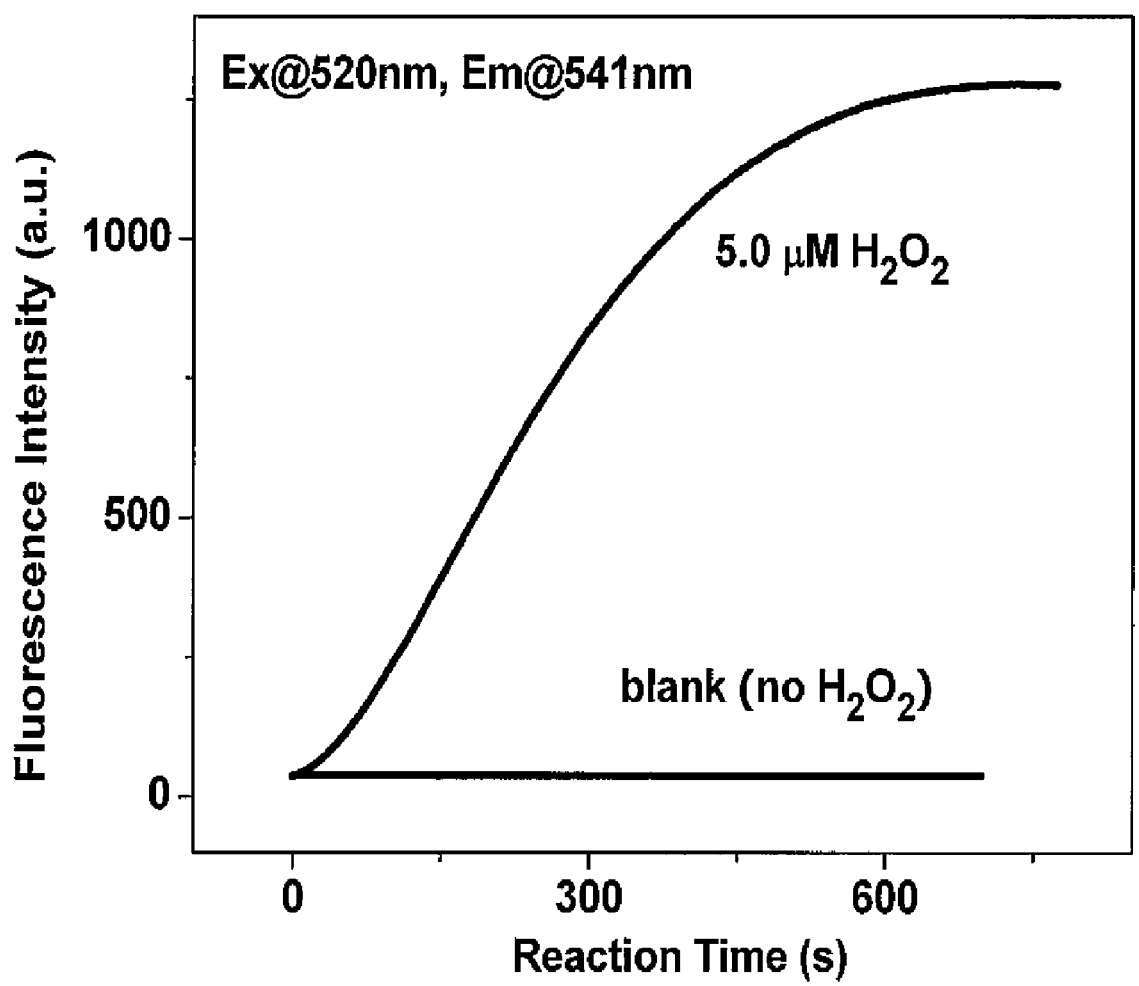
FIG. 7 depicts fluorescence spectra of a 10 μM solution of Compound 5 in an MPO/$H_2O_2$/$Cl^-$ system. Compound 5 was added to a sodium phosphate buffer (0.1 M, pH 7.4) containing MPO (1 U/100 mL) and NaCl (150 mM) at 37° C. The lower line represents the background fluorescence property of the solution in the absence of $H_2O_2$ (blank). The upper line represents the fluorescence property of the solution in the presence of $H_2O_2$ at a final concentration of 5 μM.

Hypochlorous acid in living organisms is synthesized predominantly from hydrogen peroxide and chloride ions in a reaction catalyzed by the enzyme MPO (Hidalgo, E.; Bartolome, R.; Dominguez, C., *Chem. Biol. Interact.* 2002, 139, 265-282), we applied Compound 5 to an $MPO/H_2O_2/Cl^-$ system (FIG. 7). The fluorescence intensity increased dramatically upon the addition of Compound 5 whereas almost no fluorescence was detected in the control experiment (in the absence of $H_2O_2$). Because Compound 5 does not respond to $H_2O_2$, the observed fluorescence increase may be attributed to the formation of hypochlorous acid; i.e., the hypochlorous acid probes disclosed herein can detect the production of hypochlorous acid in enzymatic systems.

Example 6

Cell Assay

Figure 8:
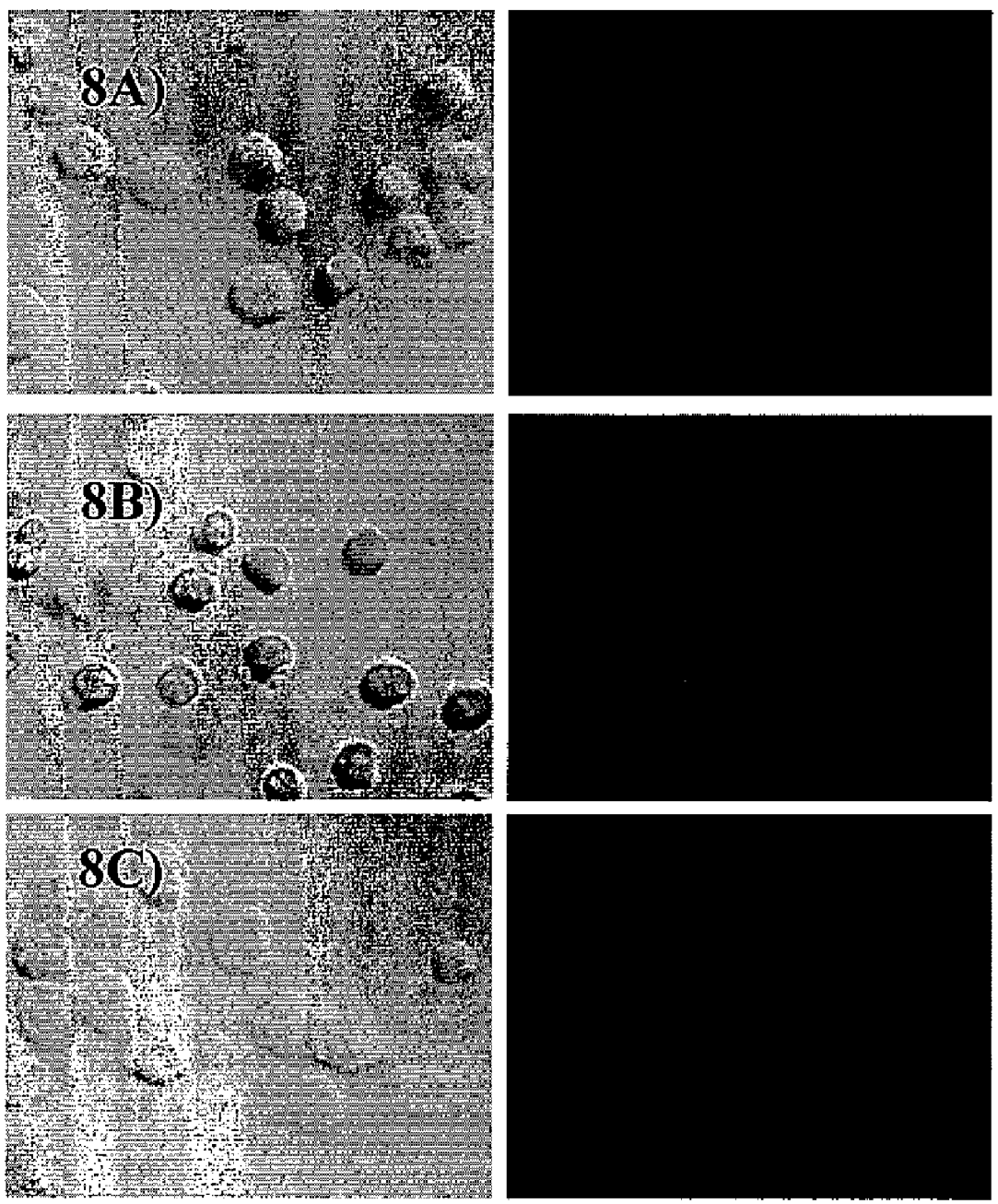
FIG. 8 depicts images of stimulated murine J774.1 macrophages that were incubated with Compound 5 at a concentration of 20 μM. The images in the left are phase contrast images whereas the images in the right are fluorescence images. The macrophages were treated with different stimulants and then incubated with Compound 5 (20 μM) for 1 hour. 8A were images of the Control without a stimulant. 8B were images of cells treated with lipopolysaccharide (LPS) (1 μg/mL) and interferon-γ (IFN-γ) (50 ng/mL) for 4 hours, then treated with PMA (10 nM) for 0.5 hours. 8C were images of cells treated with 2,2,6,6-tetramethylpiperidinooxy (TEMPO) (100 μM), LPS (1 μg/mL) and IFN-γ (50 ng/mL) for 4 hours, then treated with PMA (10 nM) for 0.5 hours. The fluorescence images were acquired 20 minutes after treating with the stimulants.

Murine J774.1 macrophages (ATCC, USA) were used to investigate the potential of Compound 5 for the detection of hypochlorous acid in living cells. First, murine J774.1 cells were stimulated with lipopolysaccharide (LPS) (1 µg/mL) and interferon-γ (IFN-γ) (50 ng/mL) for 4 hour. After incubation with Compound 5 (20 µM) for 1 hour, the cells were washed three times with PBS buffer, and further stimulated with PMA for 0.5 hours. As shown in FIG. 8A, no obvious fluorescence was observed in cells before the treatment of stimulants. It is noteworthy that fluorescent cells were observed after the treatment with LPS/IFN-γ followed by PMA (FIG. 8B). FIG. 5C shows that the fluorescence was quenched after the treatment of with 2,2,6,6-tetramethylpiperidine-1-oxyl (TEMPO). As a free radical itself, TEMPO can scavenge superoxide radical (Muijsers, R. B. R.; van den Worm, E.; Folkerts, G.; Beukelman, C. J.; Koster, A. S.; Postma, D. S.; Nijkamp, F. P., *Br. J. Pharmacol.*, 2000, 130, 932-936.), which is the precursor of hypochlorous acid. These results suggest that macrophages indeed produced OCl⁻ upon the treatment of stimulants, and the formation of hypochlorous acid can be visualized by using Compound 5.

Example 7

Cell Assay 2

Figure 9:
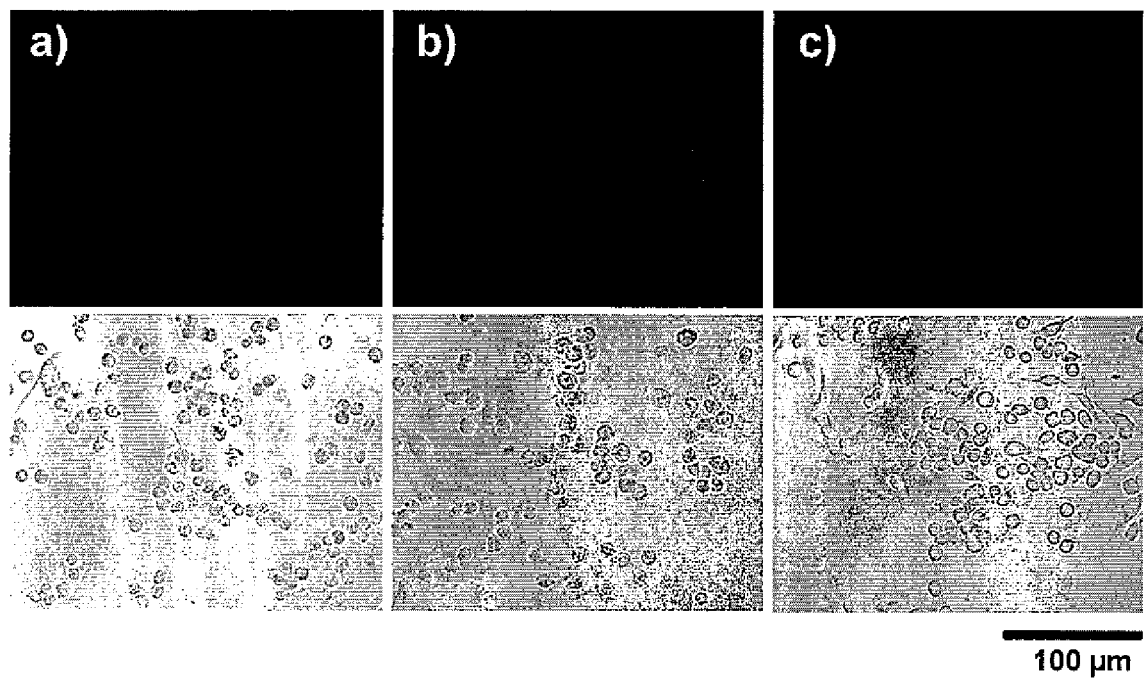
FIG. 9 depicts images of stimulated murine RAW264.7 macrophages that were incubated with Compound 5 at a concentration of 20 μM. The images in the left are phase contrast images whereas the images in the right are fluorescence images. The macrophages were treated with different stimulants and then incubated with Compound 5 (20 μM) for 1 hour. 9a were images of the Control without a stimulant. 9b were images of cells treated with lipopolysaccharide (LPS) (1 μg/mL) and interferon-γ (IFN-γ) (50 ng/mL) for 4 hours, treated with PMA (10 nM) for 0.5 hours. 9c were images of cells treated with 2,2,6,6-tetramethylpiperidinooxy (TEMPO) (100 μM), LPS (1 μg/mL) and IFN-γ (50 ng/mL) for 4 hours, then treated with PMA (10 nM) for 0.5 hours. The fluorescence images were acquired 20 minutes after treating with the stimulants.

The murine macrophage cell line RAW264.7 produces MPO upon stimulation (Adachi, Y.; Kindzelskii, A. L.; Petty, A. R.; Huang, J. B.; Maeda, N.; Yotsumoto, S.; Aratani, Y.; Ohno, N.; Petty, H. R., *J. Immunol.* 2006, 176, 5033-5040). In addition, exposure of macrophages to stimuli such as LPS/IFN-γ (interferon-γ) and phorbol myristate acetate (PMA) will also activate the generation of other ROS and RNS. In this experiment, RAW264.7 was used as a model to test whether Compound 5 can be used to detect OCl⁻ generated by an MPO/H$_2$O$_2$/Cl⁻ system under stimulation. We observed no obvious fluorescence in the cells prior to treatment with the stimulants (FIG. 9a). It is noteworthy that fluorescent cells appeared after treatment with LPS/IFN-γ followed by PMA (FIG. 9b). FIG. 9c indicates that the fluorescence was quenched after treatment with 2,2,6,6-tetramethylpiperidine-1-oxyl (TEMPO), a free radical that can scavenge superoxide radical. These results confirm that macrophages can produce OCl⁻ upon stimulation and that this process can be visualized using Compound 5.

As demonstrated above, embodiments disclosed herein provide various compounds that can be used as hypochlorous acid probes for detecting, measuring and/or screening hypochlorous acid. While this disclosure has been described with respect to a limited number of embodiments, the specific features of one embodiment should not be attributed to other embodiments of the invention. No single embodiment is representative of all aspects of this disclosure. In some embodiments, the compositions or methods may include numerous compounds or steps not mentioned herein. In other embodiments, the compositions or methods do not include, or are substantially free of, any compounds or steps not enumerated herein. Variations and modifications from the described embodiments exist. For example, the reagent composition disclosed herein need not comprising only the hypochlorous acid probes disclosed herein. It can comprise any type of compounds generally suitable for hypochlorous acid probes. It is noted that the methods for making and using the hypochlorous acid probes disclosed herein are described with reference to a number of steps. These steps can be practiced in any sequence. One or more steps may be omitted or combined but still achieve substantially the same results. The appended claims intend to cover all such variations and modifications as falling within the scope of this disclosure.

All publications and patent applications mentioned in this specification are herein incorporated by reference to the same extent as if each individual publication or patent application was specifically and individually indicated to be incorporated by reference. It is to be understood that this disclosure has been described in detailed by way of illustration and example in order to acquaint others skilled in the art with the invention, its principles, and its practical application. Further, the specific embodiments provided herein as set forth are not intended to be exhaustive or to limit the disclosure, and that many alternatives, modifications, and variations will be apparent to those skilled in the art in light of the foregoing examples and detailed description. Accordingly, this disclosure is intended to embrace all such alternatives, modifications, and variations that fall within the spirit and scope of the following claims. While some of the examples and descriptions above include some conclusions about the way the compounds, compositions and methods may function, the inventors do not intend to be bound by those conclusions and functions, but put them forth only as possible explanations in light of current understanding.

What is claimed is:

1. A compound of Formula (I):

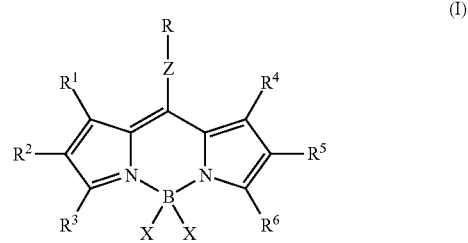

(I)

wherein X is halo;

each of R$^1$, R$^2$, R$^4$, and R$^5$ is independently hydrogen, halo, alkyl, halogenated alkyl, heteroalkyl, alkenyl, alkynyl, aryl, aralkyl, alkaryl, heterocyclyl, cycloalkyl, cycloalkenyl, cycloalkynyl, amino, alkylamino, arylamino, dialkylamino, alkylarylamino, diarylamino, hydroxy, thio, alkoxy, alkylthio, alkoxyalkyl, cyano, nitro, sulfonyl, phosphonyl, sulfonate ester, phosphate ester, —C(=O)—Y or —C(=O)-Q-Y; and each of R$^3$ and R$^6$ is independently hydrogen, halo, halogenated alkyl, heteroalkyl, alkenyl, alkynyl, aralkyl, alkaryl, heterocyclyl, cycloalkyl, cycloalkenyl, cycloalkynyl, amino, alkylamino, arylamino, dialkylamino, alkylarylamino, diarylamino, hydroxy, thio, alkoxy, alkylthio, alkoxyalkyl, cyano, nitro, sulfonyl, phosphonyl, sulfonate ester, phosphate ester, —C(=O)—Y or —C(=O)-Q-Y;

wherein Y is hydrogen, halo, alkoxy, hydroxy, thio, alkyl, alkenyl, alkynyl, cycloalkyl, cycloalkenyl, cycloalkynyl, aryl, alkaryl, arylalkyl, carbamate, amino, alkylamino, arylamino, dialkylamino, alkylarylamino, diarylamino, alkylthio, heteroalkyl, or heterocyclyl having from 3 to 7 ring atoms; and Q is alkylene, alkenylene, alkynylene, arylene, aralkylene or alkarylene, or R$^1$ and R$^2$ or R$^2$ and R$^3$ or R$^4$ and R$^5$ or R$^5$ and R$^6$ together form a 5-, 6-, or 7-membered cycloalkyl, cycloalkenyl, aryl, heteroalkyl or heteroaryl ring;

Z is a bond or a divalent linking group;

R has one of Formulae (IIIA), (IVA) and (VA):

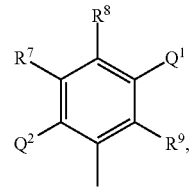

(IIIA)

-continued

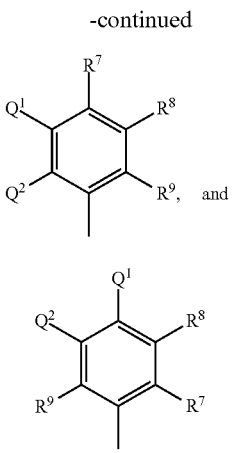

(IVA)

(VA)

wherein each of $R^7$, $R^8$ and $R^9$ is independently hydrogen, halo, alkyl, halogenated alkyl, alkenyl, alkynyl, aryl, aralkyl, alkaryl, heterocyclyl, cycloalkyl, cycloalkenyl, cycloalkynyl, hydroxy, thio, alkoxy, alkylthio, alkoxyalkyl, cyano, nitro, carboxyl, acyl, carbamate, amido, amino, alkylamino, arylamino, dialkylamino, alkylarylamino, diarylamino, or heteroalkyl, or $R^7$ and $R^8$ of Formula (IIIA), (IVA) or (VA) or $R^8$ and $R^9$ of Formula (IVA) together form a 5-, 6-, or 7-membered cycloalkyl, cycloalkenyl, aryl, heteroalkyl or heteroaryl ring; and each of $Q^1$ and $Q^2$ is independently amino or —O-$Q^3$, where $Q^3$ is hydrogen, alkyl, alkenyl, alkoxyalkyl, cycloalkyl, cycloalkenyl, cycloalkynyl, aryl, alkaryl, arylalkyl, alkylamido, alkoxyamido, alkoxycarbonyl, halogenated alkyl or heteroalkyl, with the proviso that $Q^1$ and $Q^2$ are not both amino.

2. The compound of claim 1, wherein R is a monovalent dioxygenated aryl group having one of Formulae (IIIB), (IVB) and (VB):

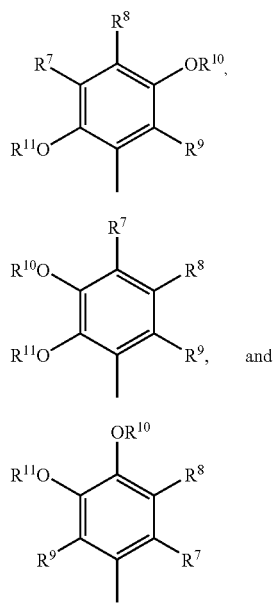

(IIIB)

(IVB)

(VB)

wherein each of $R^7$, $R^8$ and $R^9$ is independently hydrogen, halo, alkyl, halogenated alkyl, alkenyl, alkynyl, aryl, aralkyl, alkaryl, heterocyclyl, cycloalkyl, cycloalkenyl, cycloalkynyl, hydroxy, thio, alkoxy, alkylthio, alkoxyalkyl, cyano, nitro, carboxyl, acyl, carbamate, amido, amino, alkylamino, arylamino, dialkylamino, alkylarylamino, diarylamino, or heteroalkyl, or $R^7$ and $R^8$ of Formulae (IIIB)-(VB) or $R^8$ and $R^9$ of Formula (IVB) together form a 5-, 6-, or 7-membered cycloalkyl, cycloalkenyl, aryl, heteroalkyl or heteroaryl ring; and each of $R^{10}$ and $R^{11}$ is independently hydrogen, alkyl, alkenyl, alkoxyalkyl, cycloalkyl, cycloalkenyl, cycloalkynyl, aryl, alkaryl, arylalkyl, alkylamido, alkoxyamido, alkoxycarbonyl, halogenated alkyl or heteroalkyl.

3. The compound of claim 1, wherein X is F.

4. The compound of claim 1, wherein Z is a bond.

5. The compound of claim 1, wherein Z is alkylene, alkenylene, alkynylene, heteroalkylene, heteroalkenylene, heteroalkynylene, arylene, or heteroarylene.

6. The compound of claim 1, wherein $R^1$ and $R^2$ together form a 5-, 6- or 7-membered cycloalkyl, cycloalkenyl, aryl, heteroalkyl or heteroaryl ring.

7. The compound of claim 1, wherein $R^4$ and $R^5$ together form a 5-, 6- or 7-membered cycloalkyl, cycloalkenyl, aryl, heteroalkyl or heteroaryl ring.

8. The compound of claim 1, wherein $R^2$ and $R^3$ together form a 5-, 6- or 7-membered cycloalkyl, cycloalkenyl, aryl, heteroalkyl or heteroaryl ring.

9. The compound of claim 1, wherein $R^5$ and $R^6$ together form a 5-, 6- or 7-membered cycloalkyl, cycloalkenyl, aryl, heteroalkyl or heteroaryl ring.

10. A compound of Formula (I):

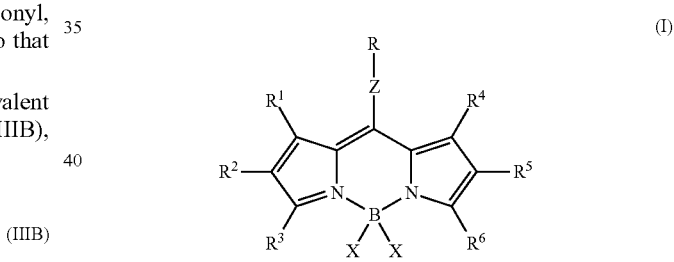

(I)

wherein each of $R^3$ and $R^6$ is independently hydrogen or —C(=O)N$R^{12}R^{13}$, wherein each of $R^{12}$ and $R^{13}$ is independently hydrogen, alkyl or aryl;

X is halo;

each of $R^1$, $R^2$, $R^4$, and $R^5$ is independently hydrogen, halo, alkyl, halogenated alkyl, heteroalkyl, alkenyl, alkynyl, aryl, aralkyl, alkaryl, heterocyclyl, cycloalkyl, cycloalkenyl, cycloalkynyl, amino, alkylamino, arylamino, dialkylamino, alkylarylamino, diarylamino, hydroxy, thio, alkoxy, alkylthio, alkoxyalkyl, cyano, nitro, sulfonyl, phosphonyl, sulfonate ester, phosphate ester, —C(=O)—Y or —C(=O)-Q-Y; and wherein Y is hydrogen, halo, alkoxy, hydroxy, thio, alkyl, alkenyl, alkynyl, cycloalkyl, cycloalkenyl, cycloalkynyl, aryl, alkaryl, aralkyl, carbamate, amino, alkylamino, arylamino, dialkylamino, alkylarylamino, diarylamino, alkylthio, heteroalkyl, or heterocyclyl having from 3 to 7 ring atoms; and Q is alkylene, alkenylene, alkynylene, arylene, aralkylene or alkarylene, or $R^1$ and $R^2$ or $R^2$ and $R^3$ or $R^4$ and $R^5$ or $R^5$ and $R^6$ together form a 5-, 6-, or 7-membered cycloalkyl, cycloalkenyl, aryl, heteroalkyl or heteroaryl ring;

Z is a bond or a divalent linking group;

R has one of Formulae (IIIA), (IVA) and (VA):

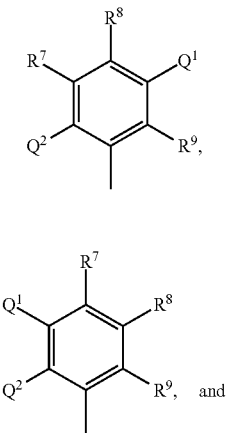

wherein each of $R^7$, $R^8$ and $R^9$ is independently hydrogen, halo, alkyl, halogenated alkyl, alkenyl, alkynyl, aryl, aralkyl, alkaryl, heterocyclyl, cycloalkyl, cycloalkenyl, cycloalkynyl, hydroxy, thio, alkoxy, alkylthio, alkoxyalkyl, cyano, nitro, carboxyl, acyl, carbamate, amido, amino, alkylamino, arylamino, dialkylamino, alkylarylamino, diarylamino, or heteroalkyl, or $R^7$ and $R^8$ of Formula (IIIA), (IVA) or (VA) or $R^8$ and $R^9$ of Formula (IVA) together form a 5-, 6-, or 7-membered cycloalkyl, cycloalkenyl, aryl, heteroalkyl or heteroaryl ring; and each of $Q^1$ and $Q^2$ is independently amino or —O-$Q^3$, where $Q^3$ is hydrogen, alkyl, alkenyl, alkoxyalkyl, cycloalkyl, cycloalkenyl, cycloalkynyl, aryl, alkaryl, aralkyl, alkylamido, alkoxyamido, alkoxycarbonyl, halogenated alkyl or heteroalkyl, with the proviso that $Q^1$ and $Q^2$ are not both amino.

11. The compound of claim 10, wherein each of $R^3$ and $R^6$ of Formula (I) is —C(=O)N$R^{12}R^{13}$, wherein each of $R^{12}$ and $R^{13}$ is alkyl.

12. The compound of claim 11, wherein each of $R^3$ and $R^6$ is —C(=O)N(CH$_2$CH$_3$)$_2$.

13. The compound of claim 1, wherein $R^7$ and $R^8$ together form a 5-, 6- or 7-membered cycloalkyl, cycloalkenyl, aryl, heteroalkyl or heteroaryl ring.

14. The compound of claim 2, wherein each of $R^{10}$ and $R^{11}$ is independently hydrogen, alkyl, alkenyl, alkoxyalkyl, cycloalkyl, cycloalkenyl, cycloalkynyl, aryl, alkaryl, arylalkyl, alkylamido, alkoxyamido, alkoxycarbonyl, halogenated alkyl or heteroalkyl.

15. The compound of claim 14, wherein $R^{10}$ is methyl and $R^{11}$ is hydrogen.

16. The compound of claim 1, wherein the compound has Formula (VI):

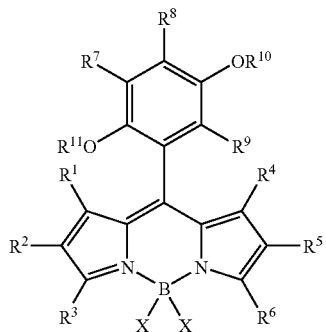

wherein X is halo;

each of $R^1$, $R^2$, $R^4$, and $R^5$ is independently hydrogen, halo, alkyl, halogenated alkyl, heteroalkyl, alkenyl, alkynyl, aryl, aralkyl, alkaryl, heterocyclyl, cycloalkyl, cycloalkenyl, cycloalkynyl, amino, alkylamino, arylamino, dialkylamino, alkylarylamino, diarylamino, hydroxy, thio, alkoxy, alkylthio, alkoxyalkyl, cyano, nitro, sulfonyl, phosphonyl, sulfonate ester, phosphate ester, —C(=O)—Y or —C(=O)-Q-Y; and each of $R^3$ and $R^6$ is independently hydrogen, halo, halogenated alkyl, heteroalkyl, alkenyl, alkynyl, aralkyl, alkaryl, heterocyclyl, cycloalkyl, cycloalkenyl, cycloalkynyl, amino, alkylamino, arylamino, dialkylamino, alkylarylamino, diarylamino, hydroxy, thio, alkoxy, alkylthio, alkoxyalkyl, cyano, nitro, sulfonyl, phosphonyl, sulfonate ester, phosphate ester, —C(=O)—Y or —C(=O)-Q-Y;

wherein Y is hydrogen, halo, alkoxy, hydroxy, thio, alkyl, alkenyl, alkynyl, cycloalkyl, cycloalkenyl, cycloalkynyl, aryl, alkaryl, arylalkyl, carbamate, amino, alkylamino, arylamino, dialkylamino, alkylarylamino, diarylamino, alkylthio, heteroalkyl, or heterocyclyl having from 3 to 7 ring atoms; and Q is alkylene, alkenylene, alkynylene, arylene, aralkylene or alkarylene, or $R^1$ and $R^2$ or $R^2$ and $R^3$ or $R^4$ and $R^5$ or $R^5$ and $R^6$ together form a 5-, 6-, or 7-membered cycloalkyl, cycloalkenyl, aryl, heteroalkyl or heteroaryl ring;

each of $R^7$, $R^8$ and $R^9$ is independently hydrogen, halo, alkyl, halogenated alkyl, alkenyl, alkynyl, aryl, aralkyl, alkaryl, heterocyclyl, cycloalkyl, cycloalkenyl, cycloalkynyl, hydroxy, thio, alkoxy, alkylthio, alkoxyalkyl, cyano, nitro, carboxyl, acyl, carbamate, amido, amino, alkylamino, arylamino, dialkylamino, alkylarylamino, diarylamino, or heteroalkyl, or $R^7$ and $R^8$ together form a 5-, 6-, or 7-membered cycloalkyl, cycloalkenyl, aryl, heteroalkyl or heteroaryl ring; and each of $R^{10}$ and $R^{11}$ is independently hydrogen, alkyl, alkenyl, alkoxyalkyl, cycloalkyl, cycloalkenyl, cycloalkynyl, aryl, alkaryl, arylalkyl, alkylamido, alkoxyamido, alkoxycarbonyl, halogenated alkyl or heteroalkyl.

17. The compound of claim 16, wherein the compound has Formula (VII) or (VIII):

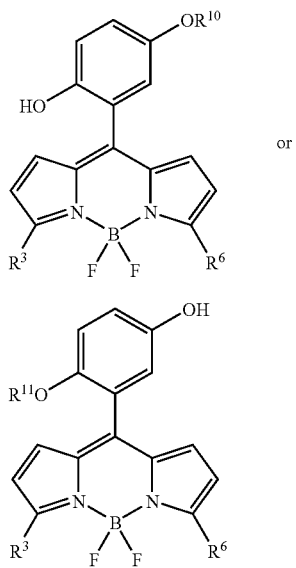

wherein $R^{10}$ is alkyl; $R^{11}$ is alkyl; and each of $R^3$ and $R^6$ is independently hydrogen or —C(=O)—Y, wherein Y is hydrogen, alkoxy, hydroxy, thio, alkyl, alkenyl, alkynyl, cycloalkyl, cycloalkenyl, cycloalkynyl, aryl, alkaryl, arylalkyl, amino, alkylamino, arylamino, dialkylamino, alkylarylamino, diarylamino, alkylthio, or 3- to 7-membered heterocyclyl ring.

18. The compound of claim 17, wherein the compound is Compound (5) or (6), or an isomer thereof:

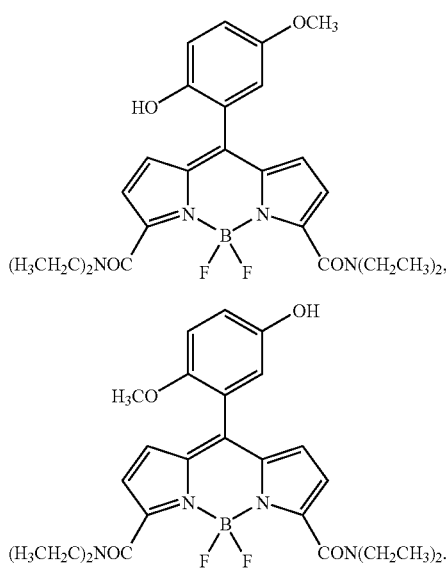

19. A composition for measuring hypochlorous acid, wherein the composition comprises the compound of claim 1.

20. The composition of claim 19, wherein the composition further comprises a solvent, an acid, a base, a buffer solution or a combination thereof.

21. A method for measuring directly or indirectly hypochlorous acid or hypochlorite in a sample, wherein the method comprises the steps of:
 a) contacting the compound of claim 1 with the sample to form a fluorescent compound; and
 b) measuring fluorescence properties of the fluorescent compound.

22. The method of claim 21, wherein the sample is a chemical sample or biological sample.

23. The method of claim 22, wherein the sample is a biological sample comprising a microorganism, or a cell or tissue from animals.

24. A high-throughput screening fluorescent method for detecting directly or indirectly hypochlorous acid or hypochlorite in samples, wherein the high-throughput method comprises the steps of:
 a) contacting the compound of claim 1 with the samples to form one or more fluorescent compounds; and
 b) measuring fluorescence properties of the fluorescent compounds to determine the amount of hypochlorous acid in the samples.

25. A high-throughput method for screening one or more target compounds that increase or decrease directly or indirectly the level of hypochlorous acid or hypochlorite, wherein the high-throughput method comprises the steps of:
 a) contacting the compound of claim 1 with the target compounds to form one or more fluorescent compounds; and
 b) measuring fluorescence properties of the fluorescent compounds to determine the target compounds qualitatively or quantitatively.

26. A method of preparing the compound of claim 1 comprising the steps of:
 a) reacting pyrroles of Formula (IXA) and (IXB):

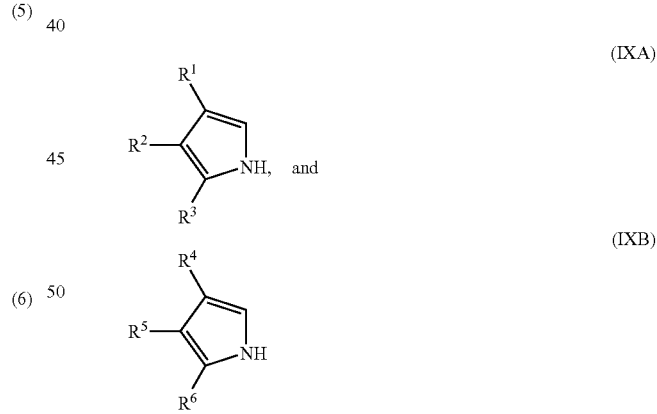

in the presence of an acid catalyst with an aldehyde of Formula (X):

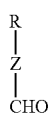

b) adding a benzoquinone to the reaction mixture to form a dipyrrole of Formula (XI):

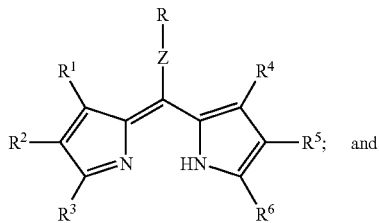
(XI)

c) reacting the dipyrrole of Formula (XI) with a boron trihalide having formula $BX_3$ and triethylamine, wherein X is halo;

each of $R^1$, $R^2$, $R^4$, and $R^5$ is independently hydrogen, halo, alkyl, halogenated alkyl, heteroalkyl, alkenyl, alkynyl, aryl, aralkyl, alkaryl, heterocyclyl, cycloalkyl, cycloalkenyl, cycloalkynyl, amino, alkylamino, arylamino, dialkylamino, alkylarylamino, diarylamino, hydroxy, thio, alkoxy, alkylthio, alkoxyalkyl, cyano, nitro, sulfonyl, phosphonyl, sulfonate ester, phosphate ester, —C(=O)—Y or —C(=O)-Q-Y; and each of $R^3$ and $R^6$ is independently hydrogen, halo, halogenated alkyl, heteroalkyl, alkenyl, alkynyl, aralkyl, alkaryl, heterocyclyl, cycloalkyl, cycloalkenyl, cycloalkynyl, amino, alkylamino, arylamino, dialkylamino, alkylarylamino, diarylamino, hydroxy, thio, alkoxy, alkylthio, alkoxyalkyl, cyano, nitro, sulfonyl, phosphonyl, sulfonate ester, phosphate ester, —C(=O)—Y or —C(=O)-Q-Y;

wherein Y is hydrogen, halo, alkoxy, hydroxy, thio, alkyl, alkenyl, alkynyl, cycloalkyl, cycloalkenyl, cycloalkynyl, aryl, alkaryl, arylalkyl, carbamate, amino, alkylamino, arylamino, dialkylamino, alkylarylamino, diarylamino, alkylthio, heteroalkyl, or heterocyclyl having from 3 to 7 ring atoms; and Q is alkylene, alkenylene, alkynylene, arylene, aralkylene or alkarylene;

Z is a bond or a divalent linking group;

R has one of Formulae (IIIA), (IVA) and (VA):

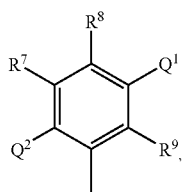
(IIIA)

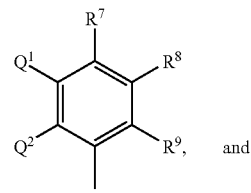
(IVA)

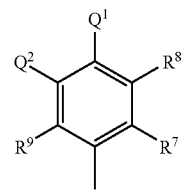
(VA)

wherein each of $R^7$, $R^8$ and $R^9$ is independently hydrogen, halo, alkyl, halogenated alkyl, alkenyl, alkynyl, aryl, aralkyl, alkaryl, heterocyclyl, cycloalkyl, cycloalkenyl, cycloalkynyl, hydroxy, thio, alkoxy, alkylthio, alkoxyalkyl, cyano, nitro, carboxyl, acyl, carbamate, amido, amino, alkylamino, arylamino, dialkylamino, alkylarylamino, diarylamino, or heteroalkyl, or $R^7$ and $R^8$ of Formula (IIIA), (IVA) or (VA) or $R^8$ and $R^9$ of Formula (IVA) together form a 5-, 6-, or 7-membered cycloalkyl, cycloalkenyl, aryl, heteroalkyl or heteroaryl ring; and each of $Q^1$ and $Q^2$ is independently amino or —O-$Q^3$, where $Q^3$ is hydrogen, alkyl, alkenyl, alkoxyalkyl, cycloalkyl, cycloalkenyl, cycloalkynyl, aryl, alkaryl, arylalkyl, alkylamido, alkoxyamido, alkoxycarbonyl, halogenated alkyl or heteroalkyl, with the proviso that $Q^1$ and $Q^2$ are not both amino.

27. The method of claim 26, wherein the reaction occurs in a solvent.

28. The method of claim 26, wherein the benzoquinone is 2,3-dichloro-5,6-dicyano-1,4-benzoquinone (DDQ).

29. The method of claim 26, wherein the acid catalyst is trifluoroacetic acid.

30. The method of claim 26, wherein the boron trihalide is $BF_3$, $BCl_3$, $BBr_3$ or a combination thereof.

31. The method of claim 26, wherein the pyrrole of Formula (IXA) is the same as the pyrrole of Formula (IXB).

* * * * *

UNITED STATES PATENT AND TRADEMARK OFFICE
CERTIFICATE OF CORRECTION

| | | |
|---|---|---|
| PATENT NO. | : 7,858,598 B2 | Page 1 of 2 |
| APPLICATION NO. | : 12/034670 | |
| DATED | : December 28, 2010 | |
| INVENTOR(S) | : Dan Yang et al. | |

It is certified that error appears in the above-identified patent and that said Letters Patent is hereby corrected as shown below:

IN THE SPECIFICATIONS:

Column 2,
Line 16, "$O_2.^-$, .OH," should read -- $O_2^{\cdot-}$, $^{\cdot}OH$--.
Line 17, "radical (ROO.)." should read --radical (ROO$^{\cdot}$).--.
Line 41, "–C(–O)–Y" should read -- –C(=O)–Y--.

Column 4,
Line 25, "$R^6$ is –C(–O)N(CH$_2$CH$_3$)$_2$." should read --$R^6$ is –C(=O)N(CH$_2$CH$_3$)$_2$.--.
Line 67, "$R^1$ and $R^2$ or $R^7$ and $R^3$ or" should read --$R^1$ and $R^2$ or $R^2$ and $R^3$ or--.

Column 5,
Line 45, "C(=O)–Y," should read -- –C(=O)–Y,--.

Column 10,
Line 43, "–CHR;" should read -- –CHO;--.

Column 11,
Line 24, "$O_2.^-$, ROO., .OH," should read --$O_2^{\cdot-}$, ROO$^{\cdot}$, $^{\cdot}OH$,--.
Line 28, "(NO.), nitrogen dioxide (NO$_2$.)," should read --(NO$^{\cdot}$), nitrogen dioxide (NO$_2^{\cdot}$),--.
Line 61, "that can used" should read --that can be used--.

Column 12,
Line 20, "$R_a$, $R_b$, $R_e$, $R^f$, $R_e$," should read --$R_a$, $R_b$, $R_c$, $R_d$, $R_e$,--.
Line 39, "phycocrythrin," should read --phycoerythrin,--.

Column 19,
Line 37, "embodiments) the" should read --embodiments, the--.
Line 52, "the $R^1$ and $R^3$" should read --the $R^2$ and $R^3$--.

Signed and Sealed this
Twenty-sixth Day of April, 2011

David J. Kappos
*Director of the United States Patent and Trademark Office*

CERTIFICATE OF CORRECTION (continued)
U.S. Pat. No. 7,858,598 B2

Column 20,
Line 63, "–C(–O)NR$^{12}$R$^{13}$" should read -- –C(=O)NR$^{12}$R$^{13}$--.

Column 22,
Line 3, "informaties" should read --informatics--.

Column 24,
Lines 2-3, "one of one of Formulae" should read --one of Formule--.

Column 31,
Line 40, "O$_2$.$^-$, .OH," should read --O$_2^{\cdot\,-}$, $^{\cdot}$OH,--.
Line 41, "(ROO.)." should read --(ROO$^{\cdot}$).--.

Column 32,
Line 62, "FIG. 5C" should read --FIG. 8C--.